(12) United States Patent
McAnelly et al.

(10) Patent No.: US 10,166,118 B2
(45) Date of Patent: *Jan. 1, 2019

(54) SPIRAL ASSEMBLY TOOL

(71) Applicant: DEPUY SYNTHES PRODUCTS, INC., Raynham, MA (US)

(72) Inventors: Jeffrey A. McAnelly, Columbia City, IN (US); Rodney E. Satterthwaite, Huntington, IN (US); Daniel E. Lashure, Fort Wayne, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 286 days.

This patent is subject to a terminal disclaimer.

(21) Appl. No.: 14/788,865

(22) Filed: Jul. 1, 2015

(65) Prior Publication Data

US 2015/0297360 A1 Oct. 22, 2015

Related U.S. Application Data

(63) Continuation of application No. 13/655,015, filed on Oct. 18, 2012, now Pat. No. 9,101,495, which is a
(Continued)

(51) Int. Cl.
 *B23P 19/04* (2006.01)
 *A61F 2/46* (2006.01)
(Continued)

(52) U.S. Cl.
 CPC .. *A61F 2/4637* (2013.01); *A61F 2002/30332* (2013.01); *A61F 2002/30604* (2013.01);
(Continued)

(58) Field of Classification Search
 CPC .......... A61F 2/4637; A61F 2002/30332; A61F 2002/4629; A61F 2002/3674;
(Continued)

(56) References Cited

U.S. PATENT DOCUMENTS

| 422,013 A | 2/1890 | Ekstrom |
| 650,795 A | 5/1900 | Maxwell |

(Continued)

FOREIGN PATENT DOCUMENTS

| DE | 3023942 A1 | 1/1982 |
| DE | 3538654 A1 | 4/1987 |

(Continued)

OTHER PUBLICATIONS

Depuy Orthopaedics, Inc., "S-Rom Modular Hip System, Minimally Invasive Calcar Miller Surgical Technique," 0612-04-503, 2004, Depuy Orthopaedics, Inc.

(Continued)

*Primary Examiner* — David Bryant
*Assistant Examiner* — Nirvana Deonauth

(57) ABSTRACT

An assembly tool for assembly of a first component of a prosthesis to a second component of the prosthesis for use in joint arthroplasty. The tool includes a first member operably associated with the first component and a second member operably associated with the second component. The second member includes a cap having a threaded recess and further includes a threaded rod adapted to engage the threaded recess so as to move the second member relative to the first member and the threaded rod is made of a harder metal than the threaded recess.

14 Claims, 14 Drawing Sheets

Related U.S. Application Data continuation-in-part of application No. 12/815,915, filed on Jun. 15, 2010, now Pat. No. 8,533,921.

(51) Int. Cl.
  *A61F 2/30* (2006.01)
  *A61F 2/36* (2006.01)

(52) U.S. Cl.
  CPC ............ *A61F 2002/3652* (2013.01); *A61F 2002/3674* (2013.01); *A61F 2002/4629* (2013.01); *A61F 2002/4642* (2013.01); *A61F 2220/0033* (2013.01); *Y10T 29/49826* (2015.01); *Y10T 29/53* (2015.01); *Y10T 29/5383* (2015.01); *Y10T 29/53796* (2015.01); *Y10T 29/53883* (2015.01)

(58) Field of Classification Search
  CPC .... A61F 2002/3652; A61F 2002/30604; A61F 2002/4642; A61F 2220/0033; A61F 2/4607; Y10T 29/5383; Y10T 29/53883; Y10T 29/49826; Y10T 29/53796; Y10T 29/53; Y10T 403/11
  See application file for complete search history.

(56) References Cited

U.S. PATENT DOCUMENTS

| | | |
|---|---|---|
| 742,521 A | 10/1903 | Terry |
| 784,243 A | 3/1905 | Whalley |
| 1,029,402 A | 6/1912 | Ritter |
| 1,241,846 A | 10/1917 | Grons |
| 1,383,304 A | 7/1921 | Hughes |
| 1,423,649 A | 7/1922 | Daniel |
| 1,534,692 A | 4/1925 | Davis |
| 1,661,682 A | 3/1928 | Scherner |
| 2,234,824 A | 3/1941 | Kingston |
| 2,248,054 A | 7/1941 | Becker |
| 2,487,331 A | 11/1949 | Greene |
| 2,626,023 A | 1/1953 | Lear |
| 2,631,584 A | 3/1953 | Purificato |
| 2,661,033 A | 12/1953 | Daniel |
| 2,711,196 A | 6/1955 | Daniel |
| 2,834,099 A | 5/1958 | Gasper |
| 2,834,382 A | 5/1958 | Daniel |
| 2,856,637 A | 10/1958 | Daniel |
| 2,864,282 A | 12/1958 | Daniel |
| 2,877,936 A | 3/1959 | Michel |
| 2,895,154 A | 7/1959 | Belcher |
| 2,902,596 A | 9/1959 | Rockwell |
| 2,914,224 A | 11/1959 | Michel |
| 2,944,373 A | 7/1960 | Mentley |
| 2,955,905 A | 10/1960 | Davies |
| 2,957,610 A | 10/1960 | Michel |
| 2,974,699 A | 3/1961 | Boles |
| 2,975,944 A | 3/1961 | Michel |
| 2,977,726 A | 4/1961 | Daniel |
| 2,981,035 A | 4/1961 | Mentley |
| 2,994,461 A | 8/1961 | Michel |
| 2,994,988 A | 8/1961 | Mentley |
| 3,048,307 A | 8/1962 | Michel |
| 3,059,278 A | 10/1962 | Daniel |
| 3,071,862 A | 1/1963 | Daniel |
| 3,077,877 A | 2/1963 | Daniel |
| 3,092,934 A | 6/1963 | Daniel |
| 3,092,935 A | 6/1963 | Daniel |
| 3,101,875 A | 8/1963 | Michel |
| 3,135,136 A | 6/1964 | Mentley |
| 3,177,507 A | 4/1965 | Becker |
| 3,180,532 A | 4/1965 | Michel |
| 3,200,484 A | 8/1965 | Garman |
| 3,220,311 A | 11/1965 | Anthony |
| 3,250,745 A | 5/1966 | Davis |
| 3,293,987 A | 12/1966 | Daniel |
| 3,300,833 A | 1/1967 | Daniel |
| 3,301,134 A | 1/1967 | Daniel |
| 3,319,526 A | 5/1967 | Daniel |
| 3,331,115 A | 7/1967 | Daniel |
| 3,335,639 A | 8/1967 | Daniel |
| 3,424,783 A | 1/1969 | Harper |
| 3,443,478 A | 5/1969 | Daniel |
| 3,451,111 A | 6/1969 | Daniel |
| 3,479,387 A | 11/1969 | Daniels |
| 3,479,388 A | 11/1969 | Daniels |
| 3,483,175 A | 12/1969 | Harper |
| 3,494,752 A | 2/1970 | Daniel |
| 3,499,920 A | 3/1970 | Daniels |
| 3,541,868 A | 11/1970 | Hall |
| 3,580,027 A | 5/1971 | Daniel |
| 3,580,029 A | 5/1971 | Daniel |
| 3,604,235 A | 9/1971 | Motz |
| 3,629,981 A | 12/1971 | McCaffery |
| 3,631,703 A | 1/1972 | Bregi |
| 3,633,583 A | 1/1972 | Fishbein |
| 3,668,139 A | 6/1972 | Daniels |
| 3,673,887 A | 7/1972 | Daniel |
| 3,679,728 A | 7/1972 | Morgan |
| 3,679,729 A | 7/1972 | Daniels |
| 3,691,718 A | 9/1972 | Woodruff |
| 3,700,957 A | 10/1972 | Daniels |
| 3,705,513 A | 12/1972 | Daniel |
| 3,749,365 A | 7/1973 | Van Gompel |
| 3,754,586 A | 8/1973 | Daniels |
| 3,810,312 A | 5/1974 | Carson |
| 3,849,322 A | 11/1974 | Wendler |
| 3,862,483 A | 1/1975 | Kloster |
| 3,869,394 A | 3/1975 | Daniels |
| 3,889,558 A | 6/1975 | Duncan |
| 3,912,727 A | 10/1975 | Daniels |
| 3,987,499 A | 10/1976 | Scharbach |
| 4,004,581 A | 1/1977 | Heimke |
| 4,009,712 A | 3/1977 | Burstein |
| 4,035,988 A | 7/1977 | Daniels |
| 4,051,559 A | 10/1977 | Pifferi |
| D246,507 S | 11/1977 | Danielson |
| 4,115,875 A | 9/1978 | Rambert |
| 4,116,200 A | 9/1978 | Braun |
| 4,150,909 A | 4/1979 | Hibarger |
| D257,533 S | 11/1980 | Bevilacqua |
| D258,957 S | 4/1981 | Bevilacqua |
| 4,305,394 A | 12/1981 | Bertuch, Jr. |
| D266,768 S | 11/1982 | Bevilacqua |
| D267,151 S | 12/1982 | Bruce |
| 4,398,074 A | 8/1983 | Danielson |
| 4,420,864 A | 12/1983 | Hoyt |
| 4,457,306 A | 7/1984 | Borzone |
| 4,458,420 A | 7/1984 | Davis |
| D275,006 S | 8/1984 | Danielson |
| 4,473,070 A | 9/1984 | Matthews |
| 4,538,886 A | 9/1985 | Townsend |
| D282,246 S | 1/1986 | Thomas |
| D282,350 S | 1/1986 | Thomas |
| 4,601,289 A | 7/1986 | Chiarizzio |
| D285,073 S | 8/1986 | Danielson |
| D285,198 S | 8/1986 | Danielson |
| 4,608,055 A | 8/1986 | Morrey |
| D286,198 S | 10/1986 | Bancroft |
| D286,285 S | 10/1986 | Danielson |
| D287,494 S | 12/1986 | Danielson |
| D289,155 S | 4/1987 | Brooks |
| 4,658,808 A | 4/1987 | Link |
| D290,399 S | 6/1987 | Kitchens |
| 4,670,015 A | 6/1987 | Freeman |
| 4,686,971 A | 8/1987 | Harris |
| 4,686,978 A | 8/1987 | Wadsworth |
| 4,693,724 A | 9/1987 | Rhenter |
| 4,710,946 A | 12/1987 | Hinch |
| 4,716,894 A | 1/1988 | Lazzeri |
| 4,738,256 A | 4/1988 | Freeman |
| 4,777,942 A | 10/1988 | Frey |
| 4,830,147 A | 5/1989 | Kawada |
| D303,114 S | 8/1989 | Danielson |
| D304,587 S | 11/1989 | Danielson |

(56) References Cited

U.S. PATENT DOCUMENTS

| | | |
|---|---|---|
| 4,891,545 A | 1/1990 | Capek |
| 4,917,530 A | 4/1990 | Engelhardt |
| 4,923,422 A | 5/1990 | Capek |
| 4,938,773 A | 7/1990 | Strand |
| 4,959,066 A | 9/1990 | Dunn |
| 4,969,911 A | 11/1990 | Greene |
| D313,233 S | 12/1990 | Andrews, Sr. |
| D315,343 S | 3/1991 | Andrews |
| 4,997,621 A | 3/1991 | Johansson |
| 5,002,578 A | 3/1991 | Luman |
| 5,002,581 A | 3/1991 | Paxson |
| 5,015,255 A | 5/1991 | Kuslich |
| 5,016,858 A | 5/1991 | Mitchell |
| 5,020,519 A | 6/1991 | Hayes |
| D318,051 S | 7/1991 | Danielson |
| 5,033,180 A | 7/1991 | Colson |
| D319,439 S | 8/1991 | Danielson |
| 5,047,033 A | 9/1991 | Fallin |
| 5,049,150 A | 9/1991 | Cozad |
| D320,985 S | 10/1991 | Danielson |
| 5,053,037 A | 10/1991 | Lackey |
| 5,057,112 A | 10/1991 | Sherman |
| 5,060,505 A | 10/1991 | Tury |
| 5,061,271 A | 10/1991 | Van Zile |
| 5,080,685 A | 1/1992 | Bolesky |
| D323,657 S | 2/1992 | Danielson |
| 5,099,714 A | 3/1992 | Hutchison |
| 5,100,407 A | 3/1992 | Conrad |
| 5,108,452 A | 4/1992 | DeMane |
| 5,133,588 A | 7/1992 | Hutchinson |
| 5,135,529 A | 8/1992 | Paxson |
| 5,162,626 A | 11/1992 | Hutchison |
| 5,171,055 A | 12/1992 | Hutchison |
| 5,171,244 A | 12/1992 | Caspari |
| 5,181,928 A | 1/1993 | Bolesky |
| 5,184,017 A | 2/1993 | Tury |
| 5,190,548 A | 3/1993 | Davis |
| 5,190,550 A | 3/1993 | Miller |
| 5,192,283 A | 3/1993 | Ling |
| 5,197,989 A | 3/1993 | Hinckfuss |
| 5,201,882 A | 4/1993 | Paxson |
| 5,207,680 A | 5/1993 | Dietz |
| 5,218,814 A | 6/1993 | Teal |
| D337,639 S | 7/1993 | Beckman |
| 5,228,459 A | 7/1993 | Caspari |
| D338,473 S | 8/1993 | Patterson |
| 5,238,267 A | 8/1993 | Hutchison |
| 5,247,171 A | 9/1993 | Wlodarczyk |
| D340,461 S | 10/1993 | Patterson |
| 5,263,498 A | 11/1993 | Caspari |
| 5,290,313 A | 3/1994 | Heldreth |
| 5,304,181 A | 4/1994 | Caspari |
| D346,979 S | 5/1994 | Stalcup |
| 5,331,124 A | 7/1994 | Danielson |
| 5,336,226 A | 8/1994 | McDaniel |
| 5,342,363 A | 8/1994 | Richelsoph |
| 5,342,366 A | 8/1994 | Whiteside |
| 5,344,423 A | 9/1994 | Dietz |
| 5,345,483 A | 9/1994 | Johansson |
| 5,352,231 A | 10/1994 | Brumfield |
| D352,521 S | 11/1994 | Sculler |
| D353,394 S | 12/1994 | Stefanski |
| 5,370,706 A | 12/1994 | Bolesky |
| 5,372,209 A | 12/1994 | Raihert |
| D355,186 S | 2/1995 | Danielson |
| D355,187 S | 2/1995 | Danielson |
| 5,387,218 A | 2/1995 | Meswania |
| 5,395,376 A | 3/1995 | Caspari |
| D357,315 S | 4/1995 | Dietz |
| 5,403,320 A | 4/1995 | Luman |
| 5,405,404 A | 4/1995 | Gardner |
| 5,409,492 A | 4/1995 | Jones |
| 5,415,659 A | 5/1995 | Lee |
| 5,420,910 A | 5/1995 | Rudokas |
| D359,064 S | 6/1995 | Sculler |
| 5,422,478 A | 6/1995 | Wlodarczyk |
| 5,457,100 A | 10/1995 | Daniel |
| 5,459,294 A | 10/1995 | Danielson |
| D364,621 S | 11/1995 | Clarke |
| 5,468,243 A | 11/1995 | Halpern |
| 5,470,336 A | 11/1995 | Ling |
| 5,474,559 A | 12/1995 | Bertin |
| 5,476,466 A | 12/1995 | Barrette |
| D365,824 S | 1/1996 | Danielson |
| 5,486,180 A | 1/1996 | Dietz |
| 5,496,324 A | 3/1996 | Barnes |
| 5,507,815 A | 4/1996 | Wagner |
| 5,507,824 A | 4/1996 | Lennox |
| 5,507,830 A | 4/1996 | DeMane |
| 5,507,833 A | 4/1996 | Bohn |
| 5,519,929 A | 5/1996 | Bleckman |
| 5,527,316 A | 6/1996 | Stone |
| 5,528,640 A | 6/1996 | Johansson |
| 5,534,005 A | 7/1996 | Tokish, Jr. |
| 5,540,687 A | 7/1996 | Fairley |
| 5,540,694 A | 7/1996 | DeCarlo, Jr. |
| 5,555,551 A | 9/1996 | Rudokas |
| 5,569,255 A | 10/1996 | Burke |
| D376,527 S | 12/1996 | Apolinski |
| 5,591,233 A | 1/1997 | Kelman |
| 5,593,411 A | 1/1997 | Stalcup |
| 5,593,452 A | 1/1997 | Higham |
| 5,600,892 A | 2/1997 | Peugh |
| 5,601,563 A | 2/1997 | Burke |
| 5,601,567 A | 2/1997 | Swajger |
| 5,607,269 A | 3/1997 | Dowd |
| 5,607,431 A | 3/1997 | Dudasik |
| D379,578 S | 6/1997 | Daniels |
| 5,643,271 A | 7/1997 | Sederholm |
| 5,645,607 A | 7/1997 | Hickey |
| 5,653,714 A | 8/1997 | Dietz |
| 5,653,764 A | 8/1997 | Murphy |
| 5,653,765 A | 8/1997 | McTighe |
| 5,658,349 A | 8/1997 | Brooks |
| 5,663,993 A | 9/1997 | Danielson |
| 5,669,812 A | 9/1997 | Schockemoehl |
| 5,683,395 A | 11/1997 | Mikhail |
| D387,962 S | 12/1997 | Apolinski |
| D387,963 S | 12/1997 | Clark |
| 5,697,932 A | 12/1997 | Smith |
| 5,702,480 A | 12/1997 | Kropf |
| 5,702,487 A | 12/1997 | Averill |
| 5,420,910 B1 | 2/1998 | Rudokas |
| 5,715,672 A | 2/1998 | Schockemoehl |
| D392,534 S | 3/1998 | Degen |
| D392,866 S | 3/1998 | Degen |
| 5,725,592 A | 3/1998 | White |
| 5,728,128 A | 3/1998 | Crickenberger |
| 5,735,857 A | 4/1998 | Lane |
| 5,743,915 A | 4/1998 | Bertin |
| 5,752,972 A | 5/1998 | Hoogeboom |
| 5,755,803 A | 5/1998 | Haines |
| 5,766,261 A | 6/1998 | Neal |
| 5,769,855 A | 6/1998 | Bertin |
| 5,776,200 A | 7/1998 | Johnson |
| 5,782,921 A | 7/1998 | Colleran |
| 5,792,143 A | 8/1998 | Samuelson |
| 5,800,553 A | 9/1998 | Albrektsson |
| 5,804,886 A | 9/1998 | Danielson |
| 5,810,827 A | 9/1998 | Haines |
| 5,810,829 A | 9/1998 | Elliott |
| 5,810,830 A | 9/1998 | Noble |
| 5,824,097 A | 10/1998 | Gabriel |
| 5,849,015 A | 12/1998 | Haywood |
| 5,850,162 A | 12/1998 | Danielsons |
| 5,853,415 A | 12/1998 | Bertin |
| 5,858,020 A | 1/1999 | Johnson |
| 5,858,828 A | 1/1999 | Seliskar |
| 5,860,969 A | 1/1999 | White |
| 5,860,981 A | 1/1999 | Bertin |
| 5,876,459 A | 3/1999 | Powell |
| 5,879,354 A | 3/1999 | Haines |
| 5,879,391 A | 3/1999 | Slamin |
| 5,890,966 A | 4/1999 | Costain |

(56) References Cited

U.S. PATENT DOCUMENTS

| | | |
|---|---|---|
| 5,902,340 A | 5/1999 | White |
| 5,906,644 A | 5/1999 | Powell |
| 5,908,423 A | 6/1999 | Kashuba |
| 5,919,195 A | 7/1999 | Wilson |
| 5,923,422 A | 7/1999 | Keens |
| 5,935,172 A | 8/1999 | Ochoa |
| 5,938,701 A | 8/1999 | Hiernard |
| 5,950,121 A | 9/1999 | Kaminsky |
| 5,951,606 A | 9/1999 | Burke |
| 5,954,460 A | 9/1999 | Degen |
| 5,957,768 A | 9/1999 | Schockemoehl |
| 5,957,925 A | 9/1999 | Cook |
| 5,966,599 A | 10/1999 | Walker |
| 5,968,049 A | 10/1999 | Da Rold |
| 5,973,064 A | 10/1999 | Zhao |
| 5,976,145 A | 11/1999 | Kennefick, III |
| 5,976,147 A | 11/1999 | LaSalle |
| 5,976,188 A | 11/1999 | Dextradeur |
| 5,993,455 A | 11/1999 | Noble |
| 5,996,812 A | 12/1999 | Sokol, Jr. |
| 5,997,419 A | 12/1999 | Daniels |
| 6,013,082 A | 1/2000 | Hiernard |
| 6,045,556 A | 4/2000 | Cohen |
| 6,048,365 A | 4/2000 | Burrows |
| 6,054,895 A | 4/2000 | Danielsons |
| 6,056,084 A | 5/2000 | Schockemoehl |
| 6,056,754 A | 5/2000 | Haines |
| 6,058,301 A | 5/2000 | Daniels |
| 6,059,528 A | 5/2000 | Danielson |
| 6,063,123 A | 5/2000 | Burrows |
| 6,069,048 A | 5/2000 | Daniel |
| 6,071,311 A | 6/2000 | O'Neil |
| 6,077,783 A | 6/2000 | Allman |
| 6,080,162 A | 6/2000 | Dye |
| 6,090,146 A | 7/2000 | Rozow, III |
| 6,096,625 A | 8/2000 | Daniel |
| 6,110,179 A | 8/2000 | Flivik |
| 6,117,138 A | 9/2000 | Burrows |
| 6,120,507 A | 9/2000 | Allard |
| 6,121,147 A | 9/2000 | Daniel |
| 6,126,694 A | 10/2000 | Gray, Jr. |
| 6,139,581 A | 10/2000 | Engh |
| 6,149,687 A | 11/2000 | Gray, Jr. |
| 6,159,214 A | 12/2000 | Michelson |
| 6,162,226 A | 12/2000 | DeCarlo, Jr. |
| 6,165,177 A | 12/2000 | Wilson |
| 6,179,116 B1 | 1/2001 | Noniewicz |
| 6,179,877 B1 | 1/2001 | Burke |
| 6,181,925 B1 | 1/2001 | Kaminsky |
| 6,185,416 B1 | 2/2001 | Rudokas |
| 6,187,012 B1 | 2/2001 | Masini |
| 6,193,725 B1 | 2/2001 | Macey |
| 6,193,759 B1 | 2/2001 | Ro |
| 6,197,064 B1 | 3/2001 | Haines |
| 6,197,065 B1 | 3/2001 | Martin |
| 6,201,253 B1 | 3/2001 | Allman |
| 6,206,884 B1 | 3/2001 | Masini |
| 6,219,538 B1 | 4/2001 | Kaminsky |
| 6,224,605 B1 | 5/2001 | Anderson |
| 6,232,721 B1 | 5/2001 | Danielsons |
| 6,235,590 B1 | 5/2001 | Daniel |
| 6,238,435 B1 | 5/2001 | Meulink |
| 6,238,436 B1 | 5/2001 | Lob |
| D443,882 S | 6/2001 | Daniels |
| 6,241,847 B1 | 6/2001 | Allman |
| 6,242,978 B1 | 6/2001 | Danielsons |
| 6,258,093 B1 | 7/2001 | Edwards |
| 6,258,095 B1 | 7/2001 | Lombardo |
| 6,258,097 B1 | 7/2001 | Cook |
| 6,260,279 B1 | 7/2001 | Apolinski |
| 6,263,998 B1 | 7/2001 | Schockemoehl |
| 6,264,699 B1 | 7/2001 | Noiles |
| 6,270,502 B1 | 8/2001 | Stulberg |
| 6,281,935 B1 | 8/2001 | Twitchell |
| 6,285,871 B1 | 9/2001 | Daniels |
| 6,287,342 B1 | 9/2001 | Copf |
| 6,310,410 B1 | 10/2001 | Lin |
| D450,304 S | 11/2001 | Daniels |
| 6,316,817 B1 | 11/2001 | Seliskar |
| 6,318,651 B1 | 11/2001 | Spiering |
| 6,319,286 B1 | 11/2001 | Fernandez |
| 6,330,845 B1 | 12/2001 | Meulink |
| 6,332,886 B1 | 12/2001 | Green |
| 6,335,766 B1 | 1/2002 | Twitchell |
| 6,354,908 B2 | 3/2002 | Allman |
| 6,355,068 B1 | 3/2002 | Doubler |
| 6,355,532 B1 | 3/2002 | Seliskar |
| 6,361,563 B2 | 3/2002 | Terrill Grisoni |
| 6,366,422 B1 | 4/2002 | Daniel |
| 6,372,520 B1 | 4/2002 | Hsia |
| D457,176 S | 5/2002 | Daniels |
| 6,382,276 B1 | 5/2002 | Daniels |
| D458,947 S | 6/2002 | Svetlik |
| 6,400,415 B1 | 6/2002 | Danielsons |
| 6,406,217 B1 | 6/2002 | Daniel |
| 6,419,147 B1 | 7/2002 | Daniel |
| 6,422,562 B1 | 7/2002 | Daniel |
| 6,422,816 B1 | 7/2002 | Danielson |
| 6,428,578 B2 | 8/2002 | White |
| 6,432,110 B1 | 8/2002 | Richelsoph |
| 6,432,141 B1 | 8/2002 | Stocks |
| 6,440,139 B2 | 8/2002 | Michelson |
| D467,485 S | 12/2002 | Daniels |
| 6,488,713 B1 | 12/2002 | Hershberger |
| 6,491,696 B1 | 12/2002 | Kunkel |
| D468,180 S | 1/2003 | Bruno |
| 6,505,684 B2 | 1/2003 | Rayssiguier |
| 6,508,841 B2 | 1/2003 | Martin |
| D469,671 S | 2/2003 | Prell |
| 6,517,581 B2 | 2/2003 | Blamey |
| RE38,058 E | 4/2003 | Fallin |
| 6,565,029 B2 | 5/2003 | Zweighaft |
| 6,568,618 B1 | 5/2003 | Vanderheyden |
| 6,569,076 B1 * | 5/2003 | Larsen .............. A61N 5/1002 600/3 |
| 6,589,284 B1 | 7/2003 | Silberer |
| 6,589,285 B2 | 7/2003 | Penenberg |
| 6,600,516 B1 | 7/2003 | Danielsons |
| 6,609,900 B2 | 8/2003 | Lucke |
| 6,613,091 B1 | 9/2003 | Zdeblick |
| 6,663,616 B1 | 12/2003 | Roth |
| 6,676,706 B1 | 1/2004 | Mears |
| 6,679,917 B2 | 1/2004 | Ek |
| 6,682,568 B2 | 1/2004 | Despres, III |
| 6,692,530 B2 | 2/2004 | Doubler |
| 6,700,359 B2 | 3/2004 | Daniels |
| 6,702,854 B1 | 3/2004 | Cheal |
| 6,706,072 B2 | 3/2004 | Dwyer |
| 6,706,621 B2 | 3/2004 | Cox |
| 6,712,825 B2 | 3/2004 | Aebi |
| 6,723,129 B2 | 4/2004 | Dwyer |
| 6,740,090 B1 | 5/2004 | Cragg |
| 6,743,235 B2 | 6/2004 | Subba Rao |
| 6,744,243 B2 | 6/2004 | Daniels |
| 6,751,266 B1 | 6/2004 | Danielsons |
| 6,755,841 B2 | 6/2004 | Fraser |
| 6,770,100 B2 | 8/2004 | Draenert |
| 6,793,208 B1 | 9/2004 | Riddle, Jr. |
| D497,499 S | 10/2004 | Daniel |
| 6,811,376 B2 | 11/2004 | Arel |
| 6,812,792 B2 | 11/2004 | Mattsson |
| 6,824,552 B2 | 11/2004 | Robison |
| 6,840,944 B2 | 1/2005 | Suddaby |
| 6,846,314 B2 | 1/2005 | Shapira |
| 6,856,029 B1 | 2/2005 | Daniel |
| 6,870,160 B1 | 3/2005 | Daniel |
| 6,875,218 B2 | 4/2005 | Dye |
| 6,883,217 B2 | 4/2005 | Barrette |
| D505,611 S | 5/2005 | Daniel |
| 6,905,515 B1 | 6/2005 | Gilbertson |
| 6,911,048 B2 | 6/2005 | Fernandez |
| 6,949,101 B2 | 9/2005 | McCleary |
| 6,990,691 B2 | 1/2006 | Klotz |
| 6,997,930 B1 | 2/2006 | Jäggi |

(56) References Cited

U.S. PATENT DOCUMENTS

| | | |
|---|---|---|
| 7,001,392 B2 | 2/2006 | McGovern |
| 7,008,420 B2 | 3/2006 | Okada |
| 7,022,141 B2 | 4/2006 | Dwyer |
| 7,066,042 B2 | 6/2006 | Andrews |
| 7,074,224 B2 | 7/2006 | Daniels |
| 7,188,556 B1 | 3/2007 | Rinner |
| 7,189,242 B2 | 3/2007 | Boyd |
| 7,204,851 B2 | 4/2007 | Trieu |
| 7,297,166 B2 | 11/2007 | Dwyer |
| 7,363,838 B2 | 4/2008 | Abdelgany |
| 7,373,709 B2 | 5/2008 | Fernando |
| 7,387,635 B2 | 6/2008 | Keller |
| 7,425,214 B1 | 9/2008 | McCarthy |
| 7,431,723 B2 | 10/2008 | Hazebrouck |
| 7,468,078 B2 | 12/2008 | Sederholm |
| 7,582,092 B2 | 9/2009 | Jones |
| 7,585,329 B2 | 9/2009 | McCleary |
| 7,601,155 B2 | 10/2009 | Petersen |
| 7,641,658 B2 | 1/2010 | Shaolian |
| 8,696,758 B2 | 4/2014 | Hood |
| 8,702,807 B2 | 4/2014 | Hood |
| 8,900,246 B2 | 12/2014 | Lashure |
| 8,998,919 B2 | 4/2015 | Jones |
| 2001/0001121 A1 | 5/2001 | Lombardo |
| 2001/0007957 A1 | 7/2001 | Martin |
| 2001/0016779 A1 | 8/2001 | Lubinus |
| 2001/0021621 A1 | 9/2001 | Moore |
| 2001/0021622 A1 | 9/2001 | Allman |
| 2001/0034526 A1 | 10/2001 | Kuslich |
| 2002/0004684 A1 | 1/2002 | Thomas |
| 2002/0038148 A1 | 3/2002 | Fernandez |
| 2002/0043296 A1 | 4/2002 | Daniels |
| 2002/0058999 A1 | 5/2002 | Dwyer |
| 2002/0059000 A1 | 5/2002 | Dwyer |
| 2002/0127115 A1 | 9/2002 | Lucke |
| 2002/0133233 A1 | 9/2002 | Blamey |
| 2002/0183758 A1 | 12/2002 | Middleton |
| 2002/0195512 A1 | 12/2002 | Zweighft |
| 2003/0001551 A1 | 1/2003 | Daniels |
| 2003/0048003 A1 | 3/2003 | Daniels |
| 2003/0050645 A1 | 3/2003 | Parker |
| 2003/0071329 A1 | 4/2003 | Cox |
| 2003/0074080 A1 | 4/2003 | Murray |
| 2003/0093080 A1 | 5/2003 | Brown |
| 2003/0095368 A1 | 5/2003 | Daniels |
| 2003/0109882 A1 | 6/2003 | Shirado |
| 2003/0114933 A1 | 6/2003 | Bouttens |
| 2003/0130740 A1 | 7/2003 | Stocks |
| 2003/0149487 A1 | 8/2003 | Doubler |
| 2003/0171756 A1 | 9/2003 | Fallin |
| 2003/0171816 A1 | 9/2003 | Scifert |
| 2003/0180146 A1 | 9/2003 | Arel |
| 2003/0187449 A1 | 10/2003 | McCleary |
| 2003/0204269 A1 | 10/2003 | Gerbec |
| 2003/0220698 A1 | 11/2003 | Mears |
| 2003/0225417 A1 | 12/2003 | Fischell |
| 2003/0228033 A1 | 12/2003 | Daniel |
| 2004/0010262 A1 | 1/2004 | Parkinson |
| 2004/0010319 A1 | 1/2004 | McTighe |
| 2004/0015239 A1 | 1/2004 | Beguec |
| 2004/0017085 A1 | 1/2004 | Daniels |
| 2004/0054373 A1 | 3/2004 | Serra |
| 2004/0054419 A1 | 3/2004 | Serra |
| 2004/0058997 A1 | 3/2004 | Daniel |
| 2004/0064186 A1 | 4/2004 | McCleary |
| 2004/0066217 A1 | 4/2004 | Daniels |
| 2004/0073315 A1 | 4/2004 | Justin |
| 2004/0092951 A1 | 5/2004 | Serra |
| 2004/0111861 A1 | 6/2004 | Barrette |
| 2004/0122437 A1 | 6/2004 | Dwyer |
| 2004/0122439 A1 | 6/2004 | Dwyer |
| 2004/0122440 A1 | 6/2004 | Daniels |
| 2004/0122525 A1 | 6/2004 | Daniels |
| 2004/0130394 A1 | 7/2004 | Mattsson |
| 2004/0135233 A1 | 7/2004 | Cox |
| 2004/0147933 A1 | 7/2004 | McGovern |
| 2004/0167527 A1 | 8/2004 | Simon |
| 2004/0172138 A1 | 9/2004 | May |
| 2004/0172139 A1 | 9/2004 | Dwyer |
| 2004/0210471 A1 | 10/2004 | Luby |
| 2004/0211046 A1 | 10/2004 | Tally |
| 2004/0236342 A1 | 11/2004 | Ferree |
| 2004/0260297 A1 | 12/2004 | Padget |
| 2004/0267266 A1 | 12/2004 | Daniels |
| 2004/0267267 A1 | 12/2004 | Daniels |
| 2004/0267372 A1 | 12/2004 | Vanasse |
| 2004/0267373 A1 | 12/2004 | Dwyer |
| 2005/0004679 A1 | 1/2005 | Sederholm |
| 2005/0010992 A1 | 1/2005 | Klotz |
| 2005/0015049 A1 | 1/2005 | Rioux |
| 2005/0033444 A1 | 2/2005 | Jones |
| 2005/0047239 A1 | 3/2005 | Takahashi |
| 2005/0078289 A1 | 4/2005 | Daniel |
| 2005/0081910 A1 | 4/2005 | Danielson |
| 2005/0085820 A1 | 4/2005 | Collins |
| 2005/0115391 A1 | 6/2005 | Baker |
| 2005/0154331 A1 | 7/2005 | Christie |
| 2005/0188878 A1 | 9/2005 | Baker |
| 2005/0209597 A1 | 9/2005 | Long |
| 2005/0222572 A1 | 10/2005 | Chana |
| 2005/0234461 A1 | 10/2005 | Burdulis |
| 2005/0234462 A1 | 10/2005 | Hershberger |
| 2005/0234559 A1 | 10/2005 | Fernandez |
| 2005/0240193 A1 | 10/2005 | Layne |
| 2005/0261702 A1 | 11/2005 | Oribe |
| 2005/0267937 A1 | 12/2005 | Daniels |
| 2005/0288676 A1 | 12/2005 | Schnieders |
| 2006/0015110 A1 | 1/2006 | Pepper |
| 2006/0015112 A1 | 1/2006 | McGovern |
| 2006/0024656 A1 | 2/2006 | Morris |
| 2006/0027027 A1 | 2/2006 | Serra |
| 2006/0058810 A1 | 3/2006 | Wozencroft |
| 2006/0106393 A1 | 5/2006 | Huebner |
| 2006/0217737 A1 | 9/2006 | Iversen |
| 2006/0260440 A1 | 11/2006 | Abdelgany |
| 2007/0005144 A1 | 1/2007 | Leisinger |
| 2007/0100464 A1 | 5/2007 | Meulink |
| 2007/0123908 A1 | 5/2007 | Jones |
| 2007/0162033 A1 | 7/2007 | Daniels |
| 2007/0179502 A1 | 8/2007 | Raynor |
| 2007/0233132 A1 | 10/2007 | Valla |
| 2007/0244566 A1 | 10/2007 | Daniels |
| 2007/0260315 A1 | 11/2007 | Foley |
| 2007/0299534 A1 | 12/2007 | Lewis |
| 2008/0065081 A1 | 3/2008 | Lechot |
| 2008/0071279 A1 | 3/2008 | Bandeira |
| 2008/0077156 A1 | 3/2008 | Emstad |
| 2008/0084017 A1* | 4/2008 | Barziza ............... B23Q 3/103 269/60 |
| 2008/0091212 A1* | 4/2008 | Dwyer ................. A61F 2/36 606/99 |
| 2008/0114367 A1 | 5/2008 | Meyer |
| 2008/0133024 A1 | 6/2008 | Meswania |
| 2008/0161811 A1 | 7/2008 | Daniels |
| 2008/0188878 A1 | 8/2008 | Young |
| 2008/0275457 A1 | 11/2008 | Meek |
| 2009/0112216 A1 | 4/2009 | Leisinger |
| 2009/0112218 A1 | 4/2009 | McCleary |
| 2009/0187251 A1 | 7/2009 | Justin |
| 2009/0228012 A1 | 9/2009 | Gangji |
| 2009/0307887 A1 | 12/2009 | Jones |
| 2010/0069909 A1 | 3/2010 | Taylor |
| 2010/0107829 A1 | 5/2010 | Zimmerman |
| 2010/0145345 A1 | 6/2010 | Ammann |
| 2010/0168752 A1 | 7/2010 | Edwards |
| 2010/0249943 A1 | 9/2010 | Bergin |
| 2011/0054628 A1 | 3/2011 | Banks |
| 2011/0071527 A1 | 3/2011 | Nelson |
| 2011/0302760 A1 | 12/2011 | Leisinger |
| 2012/0053698 A1* | 3/2012 | Huff .................. A61F 2/4637 623/22.11 |
| 2012/0259341 A1 | 10/2012 | McCleary |
| 2012/0259421 A1 | 10/2012 | Satterthwaite |

(56) References Cited

U.S. PATENT DOCUMENTS

FOREIGN PATENT DOCUMENTS

| | | |
|---|---|---|
| DE | 2823406 C2 | 11/1988 |
| DE | 10014401 A1 | 6/2001 |
| DE | 20114835 U1 | 1/2002 |
| DE | 202006000845 U1 | 5/2006 |
| DE | 202012102017 U1 | 10/2013 |
| EP | 206777 A2 | 12/1986 |
| EP | 239711 A1 | 10/1987 |
| EP | 333990 A2 | 9/1989 |
| EP | 511244 A1 | 11/1992 |
| EP | 595956 A1 | 5/1994 |
| EP | 661023 A2 | 7/1995 |
| EP | 726063 A1 | 8/1996 |
| EP | 728449 A2 | 8/1996 |
| EP | 842639 A2 | 5/1998 |
| EP | 861635 A2 | 9/1998 |
| EP | 1000595 A1 | 5/2000 |
| EP | 1013245 A2 | 6/2000 |
| EP | 1080701 A2 | 3/2001 |
| EP | 1084680 A2 | 3/2001 |
| EP | 1191906 A1 | 4/2002 |
| EP | 1201191 A1 | 5/2002 |
| EP | 1263334 A2 | 12/2002 |
| EP | 1323395 A2 | 7/2003 |
| EP | 1348384 A2 | 10/2003 |
| EP | 1369089 A2 | 12/2003 |
| EP | 1435223 A1 | 7/2004 |
| EP | 1493407 A2 | 1/2005 |
| EP | 1522284 A2 | 4/2005 |
| EP | 1591084 A1 | 11/2005 |
| EP | 1080701 B1 | 8/2006 |
| EP | 1738723 A1 | 1/2007 |
| EP | 1905396 A1 | 4/2008 |
| EP | 2055273 A1 | 5/2009 |
| EP | 2057969 A2 | 5/2009 |
| FR | 2606628 A1 | 5/1988 |
| FR | 2699400 A1 | 6/1994 |
| FR | 2737107 A1 | 1/1997 |
| FR | 2828397 A1 | 2/2003 |
| FR | 2832624 A1 | 5/2003 |
| FR | 2926212 A1 | 7/2009 |
| GB | 250441 A | 6/1992 |
| JP | 5212069 A | 8/1993 |
| JP | 6500039 A | 1/1994 |
| JP | 10080095 A | 3/1998 |
| JP | 2000210314 A | 8/2000 |
| JP | 2002153479 A | 5/2002 |
| JP | 2002238912 A | 8/2002 |
| JP | 2003339724 A | 12/2003 |
| JP | 2004223261 A | 8/2004 |
| JP | 2004251450 A | 9/2004 |
| JP | 2006501917 T | 1/2006 |
| JP | 2006523106 A | 10/2006 |
| JP | 2007061154 A | 3/2007 |
| JP | 2007503911 A | 3/2007 |
| JP | 2007508063 A | 4/2007 |
| JP | 2008086773 A | 4/2008 |
| JP | 2010540179 A | 12/2010 |
| JP | 2012000460 A | 1/2012 |
| JP | 5148516 B2 | 2/2013 |
| JP | 5212069 B2 | 6/2013 |
| WO | WO 1991010408 A1 | 7/1991 |
| WO | WO 1992010138 A1 | 6/1992 |
| WO | WO 1993001769 A1 | 2/1993 |
| WO | WO 1994012123 A1 | 6/1994 |
| WO | WO 1994027507 A1 | 12/1994 |
| WO | WO 1996015738 A1 | 5/1996 |
| WO | WO 1996015739 A1 | 5/1996 |
| WO | WO 1999020196 A1 | 4/1999 |
| WO | WO 2001067997 A1 | 9/2001 |
| WO | WO 2002102254 A2 | 12/2002 |
| WO | WO 2003015642 A1 | 2/2003 |
| WO | WO 2003065906 A2 | 8/2003 |
| WO | WO 2003082159 A1 | 10/2003 |
| WO | WO 2003092513 A1 | 11/2003 |
| WO | WO 2003094698 A2 | 11/2003 |
| WO | WO 2003094803 A1 | 11/2003 |
| WO | WO 2004028266 A1 | 4/2004 |
| WO | WO 2004032767 A1 | 4/2004 |
| WO | WO 2004089224 A2 | 10/2004 |
| WO | WO 2005034817 A1 | 4/2005 |
| WO | WO 2007026119 A1 | 3/2007 |
| WO | WO 2007098549 A1 | 9/2007 |
| WO | WO 2007106752 A2 | 9/2007 |
| WO | WO 2008069800 A1 | 6/2008 |
| WO | WO 2009024798 A1 | 2/2009 |
| WO | WO 2012138824 A2 | 10/2012 |

OTHER PUBLICATIONS

Engage Modular Revision Hip System: Surgical Technique, 2007, DePuy Orthopaedics, Inc, 19 pages.

Gray, John R.; Clinically-Oriented Geometry of the Femur; A thesis submitted to the School of Physical & Health Education in partial fulfillment of requirements for the degree of Master of Science, Queen's University, Kingston, Ontario, Canada, Aug. 1995, 73 pages.

Paul, H.A., et al. "Development of a Surgical Robot for Cementless Total Hip Arthroplasty," Clinical Orthopedics & Related Research 285 Dec. 1992: 57-66.

S-Rom Modular Hip System, retrieved from Johnson & Johnson Gateway web site http://www.jnj.gateway.com/home.jhtml?loc=USENG&page-viewContent&contented=fc0de0010000030, retrieved on Sep. 26, 2005, 1 page.

Zimmer Fracture Equipment & Orthopaedic Appliances, 1 page, published at least as early as Sep. 29, 2005.

Zimmer Metasul LDH Large Diameter Head; Surgical Technique Enhancing Stability and Increasing Range of Motion, available at least as early as Sep. 28, 2006 (19 pages).

* cited by examiner

SPIRAL ASSEMBLY TOOL

CROSS-REFERENCE TO RELATED APPLICATIONS

This is a continuation of U.S. application Ser. No. 13/655,015, filed Oct. 18, 2012, which is a continuation-in-part application of and claims priority to U.S. Pat. No. 8,533,921, of the same title, filed on Jun. 15, 2010 and granted on Sep. 17, 2013, which is incorporated by reference herein in its entirety.

TECHNICAL FIELD

The present invention relates generally to the field of orthopaedics, and more particularly, to an implant for use in arthroplasty.

BACKGROUND

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

Many designs and methods for manufacturing implantable articles, such as bone prostheses, are known. Such bone prostheses include components of artificial joints such as elbows, hips, knees and shoulders.

During performance of a joint replacement procedure, it is generally necessary to provide the surgeon with a certain degree of flexibility in the selection of a prosthesis. In particular, the anatomy of the bone into which the prosthesis is to be implanted may vary somewhat from patient to patient. Such variations may be due to, for example, the patient's age, size and gender. For example, in the case of a femoral prosthesis, the patient's femur may be relatively long or relatively short thereby requiring use of a femoral prosthesis which includes a stem that is relatively long or short, respectively. Moreover, in certain cases, such as when use of a relatively long stem length is required, the stem must also be bowed in order to conform to the anatomy of the patient's femoral canal.

Such a need for prostheses of varying shapes and sizes thus creates a number of problems in regard to the use of a one-piece prosthesis. For example, a hospital or surgery center must maintain a relatively large inventory of prostheses in order to have the requisite mix of prostheses needed for certain situations, such as trauma situations and revision surgery. Moreover, since the bow of the stem must conform to the bow of the intramedullary canal of the patient's femur, rotational positioning of the upper portion of the prosthesis is limited, thereby rendering precise location of the upper portion and hence the head of the prosthesis very difficult. In addition, since corresponding bones of the left and right side of a patient's anatomy (e.g. left and right femur) may bow in opposite directions, it is necessary to provide (left) and (right) variations of the prosthesis in order to provide anteversion of the bone stem, thereby further increasing the inventory of prostheses which must be maintained.

As a result of these and other drawbacks, a number of modular prostheses have been designed. As its name implies, a modular prosthesis is constructed in modular form so that the individual elements or figures of the prosthesis can be selected to fit the needs of a given patient's anatomy. For example, modular prostheses have been designed which include a proximal neck component which can be assembled to any one of numerous distal stem components in order to create an assembly which fits the needs of a given patient's anatomy. Such a design allows the distal stem component to be selected and thereafter implanted in the patient's bone in a position which conforms to the patient's anatomy while also allowing for a limited degree of independent positioning of the proximal neck component relative to the patient's pelvis.

One issue that arises as a result of the use of a modular prosthesis is the locking of the components relative to one another. In particular, firm, reproducible, locking of the proximal neck component to the distal stem component is critical to prevent separation of the two components subsequent to implantation thereof into the patient. The need for the firm locking is particularly necessary if the design does not provide for positive locking with weight bearing. As such, a number of locking mechanisms have heretofore been designed to lock the components of a modular prosthesis to one another. For example, a number of modular prostheses have heretofore been designed to include a distal stem component which has an upwardly extending post which is received into a bore defined distal neck component. A relatively long fastener such as a screw or bolt is utilized to secure the post with the bore. Other methods of securing modular components include the impacting of one component onto the other. This method has highly variable results.

Current designs of modular stems include designs in which the modular connection utilizes a tapered fit between the two components. For example, the proximal body may include an internal taper which mates with an external taper on the distal stem. Such a taper connection may be used in conjunction with additional securing means, for example, a threaded connection or may be used alone. It is important that the tapered connection be secure. For example, the proper amount of force must be applied to the tapered connection to properly secure the tapered connection so that the connection can withstand the forces associated with the operation of the stem.

Current attempts to provide a device to adjoin components of a modular joint prosthesis are fraught with several problems. For example, the device may not provide sufficient mechanical advantage to securely lock the components. Further, the ergonomics available to lock the components may not be optimal. There is thus a need to provide for an assembly tool capable of alleviating at least some of the aforementioned problems.

SUMMARY

According to one embodiment of the present invention, an assembly tool for assembly of a first component of a prosthesis to a second component of the prosthesis for use in joint arthroplasty is provided. The tool includes a first member operably associated with the first component. The first member defines a first member longitudinal axis thereof. A second member is operably associated with the second component, and the second member defines a second member longitudinal axis thereof. A washer system is also included and is coupled to the second member. A drive mechanism is coupled to washer system, such that as the drive mechanism is activated, the washer system rotates about the second member longitudinal axis and expands along the second member longitudinal axis, wherein such movement further causes the second member to move relative to the first member along the second member longitudinal axis.

According to another embodiment of the present invention, a method for assembling a first component of a prosthesis to a second component of the prosthesis for use in joint arthroplasty is provided. The method includes using an assembly tool having a first member and a second member. The second member defines a second member longitudinal axis. The assembly tool also includes a washer system coupled to the second member and a drive mechanism coupled to the washer system. The first component of the prosthesis is inserted onto the second component of the prosthesis. The second member of the assembly tool is secured onto the second component of the prosthesis. The drive mechanism is activated, causing the second member to move relative to the first member along the second member longitudinal axis.

According to yet another embodiment of the present invention, an assembly tool for assembly of a first component of a prosthesis to a second component of the prosthesis for use in joint arthroplasty is provided. The tool includes a first member operably associated with the first component. The first member defines a first member longitudinal axis thereof. A second member is operably associated with the second component. The second member defines a second member longitudinal axis thereof, and the second member includes a tensile rod. A drive mechanism is coupled to the second member, such that as the drive mechanism is activated and reaches a predetermined load, the tension member breaks.

According to yet another embodiment of the invention, an assembly tool for assembly of a first component of a prosthesis to a second component of the prosthesis for use in joint arthroplasty is provided. The tool includes a first member operably associated with the first component and a second member operably associated with the second component. The second member includes a cap having a threaded recess and further includes a threaded rod adapted to engage the threaded recess so as to move the second member relative to the first member and the threaded rod is made of a harder metal than the threaded recess.

According to another embodiment of the present invention, an assembly tool for assembly of a first component of a prosthesis to a second component of the prosthesis for use in joint arthroplasty is provided. The tool includes a first member operably associated with the first component. The first member defines a first member longitudinal axis thereof. The tool further includes a second member operably associated with the second component. The second member includes a tensile bar adapted to break at a predetermined force, and the second member includes a housing adapted to retain the tensile bar after the tensile bar breaks.

BRIEF DESCRIPTION OF THE DRAWINGS

For a more complete understanding of the present invention and the advantages thereof, reference is now made to the following description taken in connection with the accompanying drawings.

DETAILED DESCRIPTION OF THE DRAWINGS

Embodiments of the present invention and the advantages thereof are best understood by referring to the following descriptions and drawings, wherein like numerals are used for like and corresponding parts of the drawings.

Figure 1:
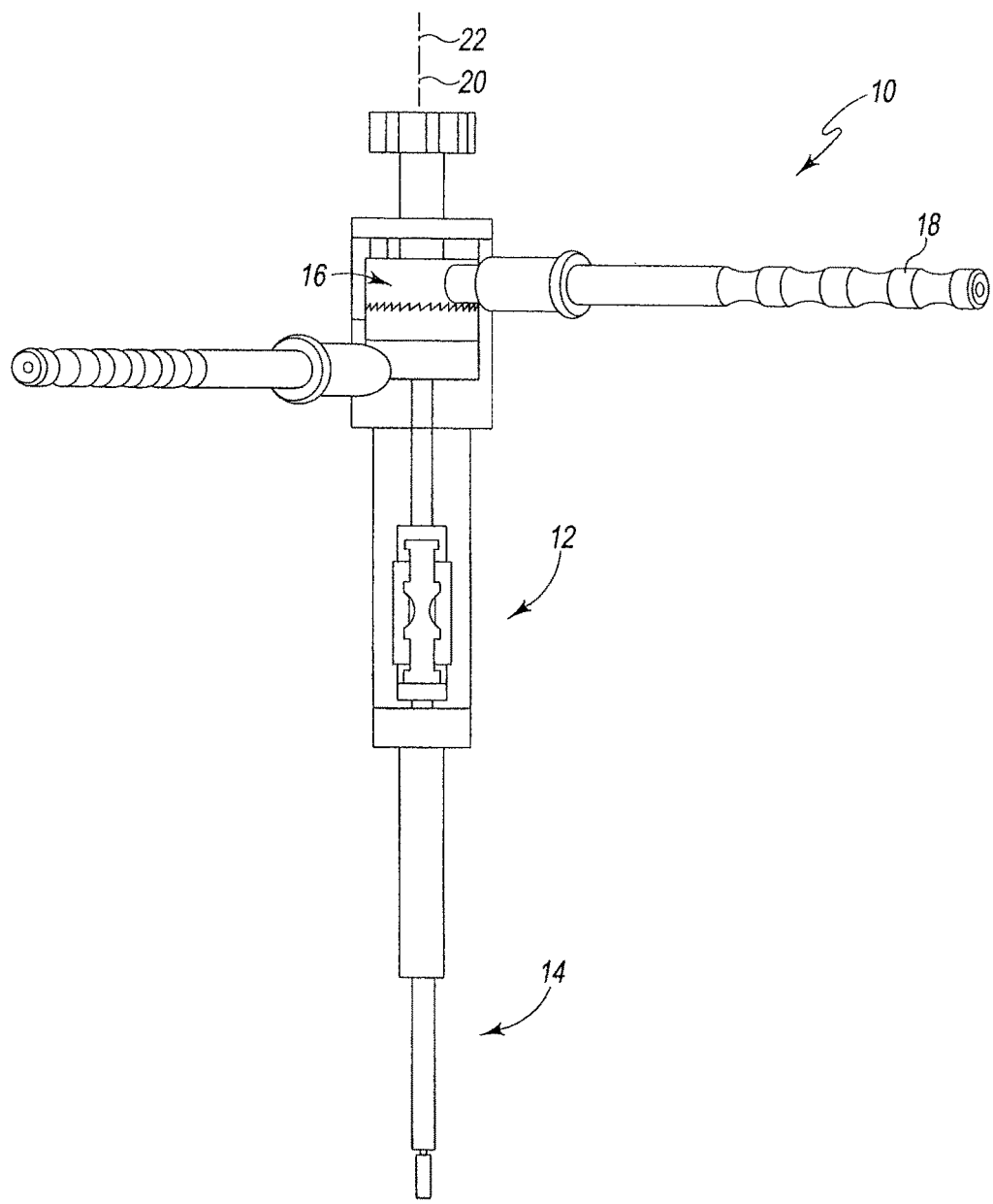
FIG. 1 is a see-through perspective view of an assembly tool according to one embodiment of the present invention.

FIG. 1 is a perspective view of an assembly tool 10 according to one embodiment of the present invention. The assembly tool 10 includes a first member 12 and a second member 14. Coupled to the second member 14 is a washer system 16. A drive mechanism 18 is coupled to the washer system 16. The first member 12 has a first member longitudinal axis 20 and the second member 14 has a second member longitudinal axis 22. In the illustrated embodiment, the first member longitudinal axis 20 and the second member longitudinal axis 22 are co-incident. In other embodiments, the two axes 20, 22 may be parallel or offset at an angle from one another. As the drive mechanism 18 is activated, it causes the washer system 16 to rotate about the second member longitudinal axis 22. In the illustrated embodiment, the drive mechanism is a handle that is ratcheted about the second member longitudinal axis 22. However, in other embodiments, it could be a longitudinal handle, a Hudson connection that connects to a power source, or other known drive mechanism that would cause the washer system 16 to rotate about the second member longitudinal axis 22.

Figure 2:
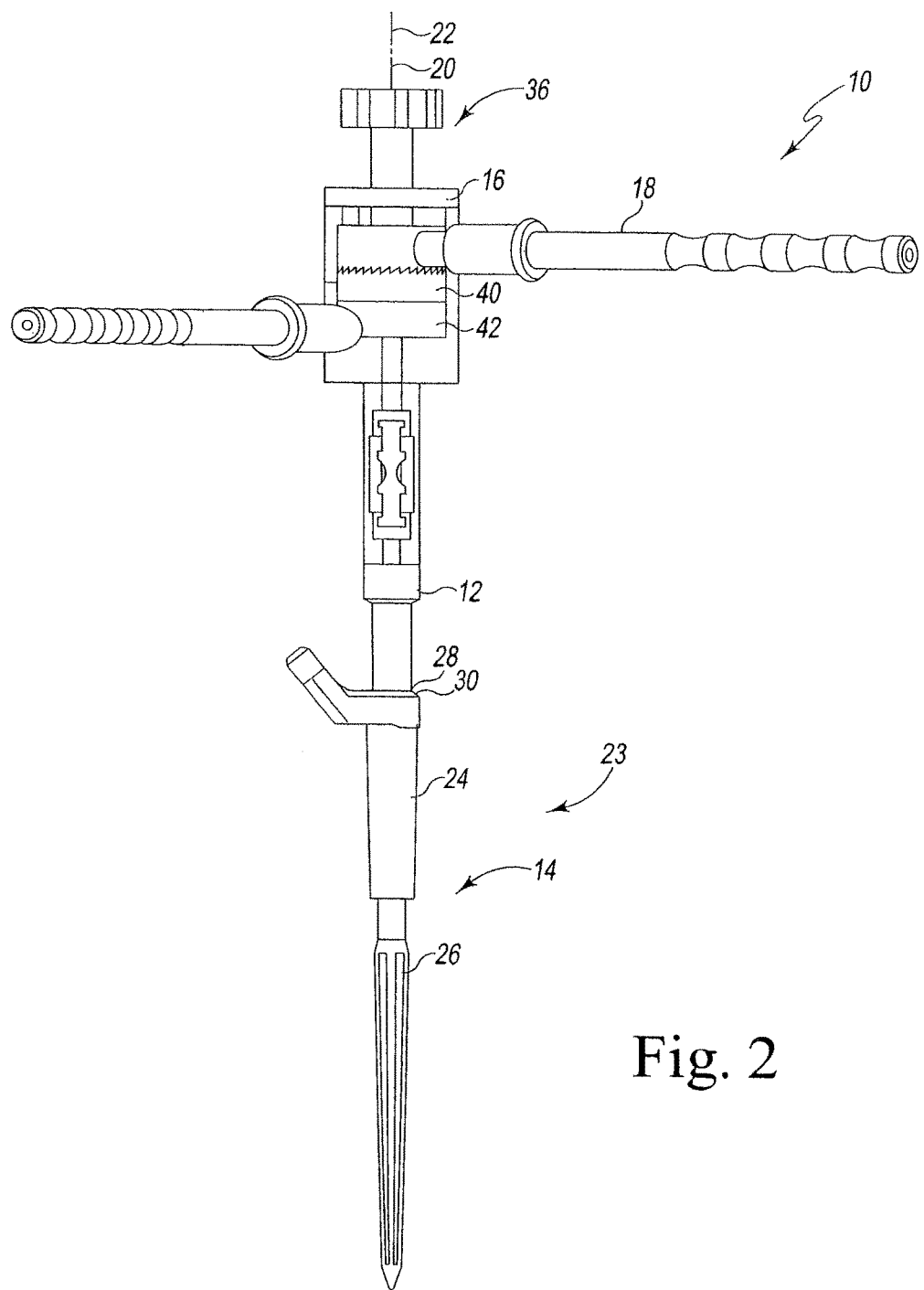
FIG. 2 is see-through view of the assembly tool of FIG. 1 coupled to a modular implant.

Referring now to FIG. 2, a see-through view of the assembly tool 10 is shown coupled to a modular implant 23. As shown, the modular implant 23 includes a first component 24 (or a proximal or neck component) and a second component 26 (or a distal or stem component). The first member 12 of the assembly tool 10 includes a distal end 28 that abuts a proximal end 30 of the neck component 24. In other embodiments, other connection means may be used. For example, the distal end 28 may include threads that engage a threaded end of the proximal end 30 of the neck component 24. Alternatively, the connection means may be a retractable button/recess system, a slotted 1-shaped recess and rod system, an undercut, an expandable collet system, or any other known engagement system.

Figure 3:
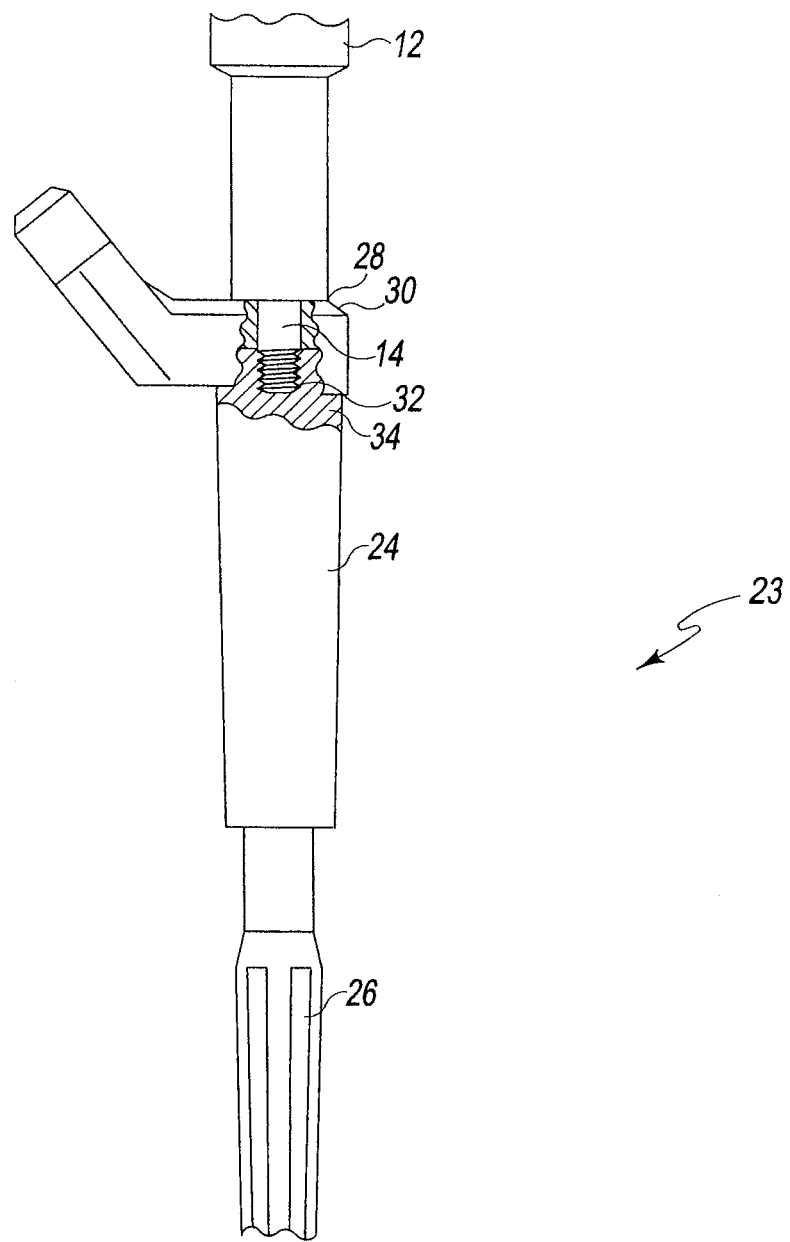
FIG. 3 is an enlarged see-through view of FIG. 2.

As shown in FIG. 3, a distal end 32 of the second member 14 engages a proximal end 34 of the stem component 26. In this embodiment, the distal end 32 of the second member 14 is threaded and fits inside a threaded bore of the proximal end 34 of the stem component 26. Alternatively, the distal end 32 of the second member 14 may have the threaded bore and the proximal end 34 of the stem component may be threaded. In other embodiments, other known means of connecting pieces may be used. For example, an expandable collet may be used. Alternatively, the connection means may be a retractable button/recess system, an undercut, a slotted 1-shaped recess and rod system, an expandable collet system, or any other known engagement system.

Figure 4:
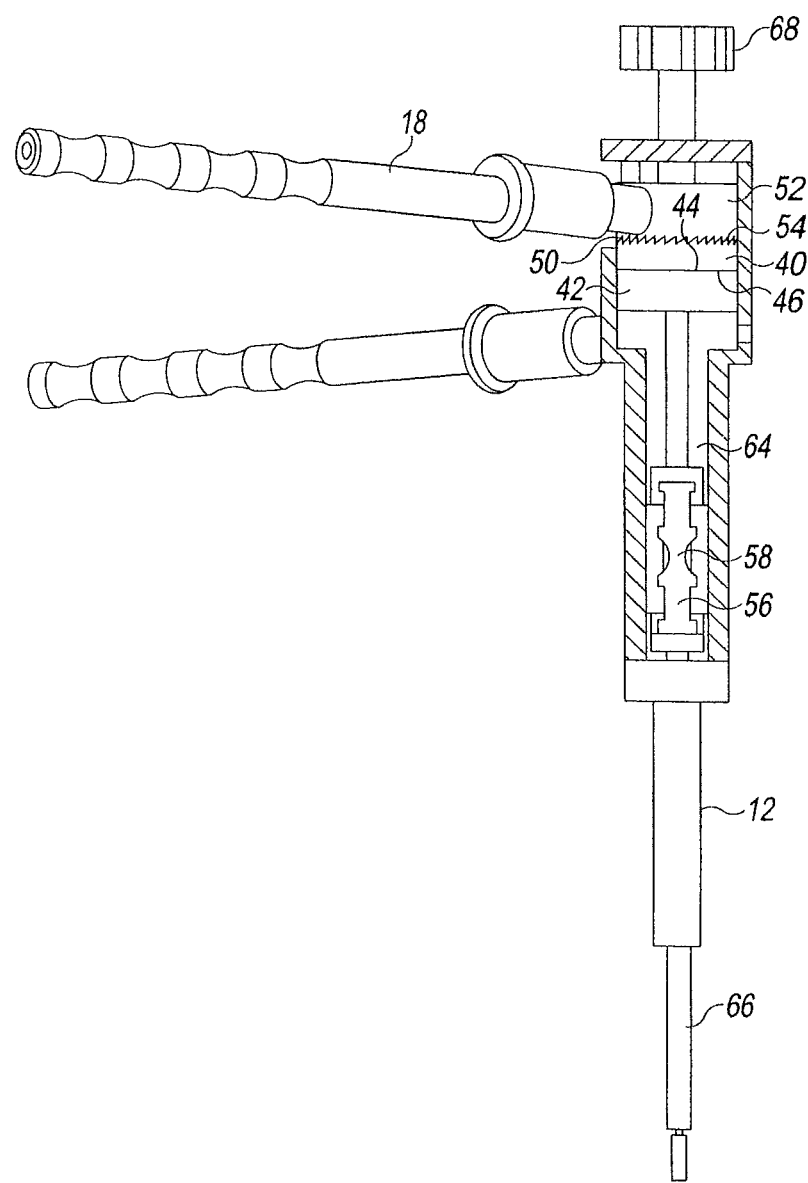
FIG. 4 is a perspective view of the assembly tool according to one embodiment of the present invention.

The second member 14 also includes a proximal end 36 (FIG. 2). The proximal end 36 includes a knob 68 (FIG. 4). The knob 68 is coupled to the threaded distal end 32, such that as the knob 68 is rotated about the second member longitudinal axis 22, the threaded distal end 32 is threaded into the threaded bore proximal end 34 of the stem component 26.

Figure 5:
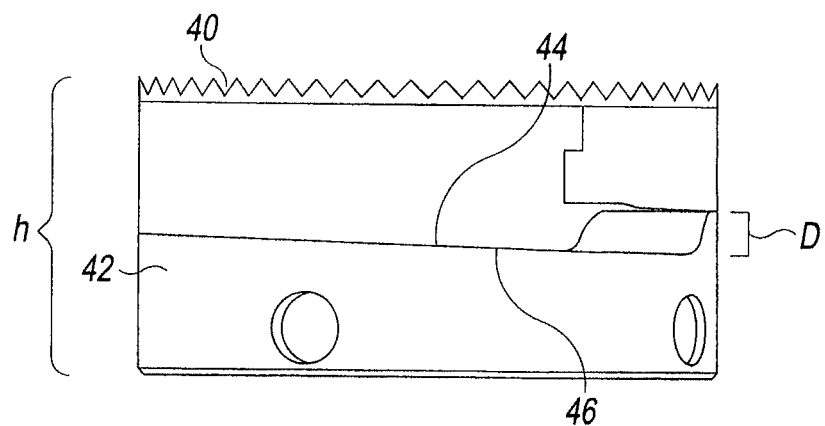
FIG. 5 is a perspective view of the washer assembly of FIG. 1.
Figure 6:
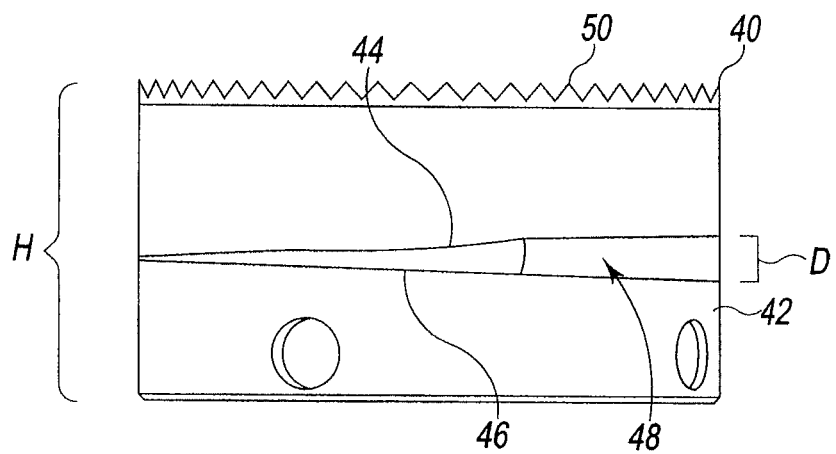
FIG. 6 is a perspective view of the washer assembly of FIG. 5 in a rotated position.

Turning now to FIGS. 4-6, the washer system 16 will be described. The washer system 16 includes a first spiral washer 40 and a second spiral washer 42. The first spiral washer 40 is coupled to the drive mechanism 18 and includes a first spiral ramp 44 and the second spiral washer 42 is coupled to the second member 14 and the first spiral washer 40 and includes a second spiral ramp 46 (FIG. 5). The first spiral ramp 44 abuts the second spiral ramp 46. The washer system 16 has an overall starting height of h. As the first spiral ramp 44 is rotated relative to the second spiral ramp 46, the ramps engage one another, creating a gap 48 between the first spiral washer 40 and the second spiral washer 42. The gap 48 is of a distance D. As shown in FIGS. 5 and 6, the washers 40, 42 begin by being flush against one another. However, as the first spiral washer 40 is rotated, the spiral ramps 44, 46 are rotated enlarging the height of the two washers 40, 42. The distance D of the gap 48 remains the same. In FIG. 6, the overall height of the washer system 16 is now H, which is larger than h. This change in height is generated by the opposing spiral ramps 44, 46 engaging one another, creating a washer system 16 with a variable height.

As shown in FIG. 4, the first washer 40 includes a ratchet end 50 that opposes the spiral ramp 44. The first washer 40 is coupled to a ratchet washer 52. The ratchet washer 52 is connected to the handle 18. One side 54 of the ratchet washer 52 is ratcheted and mates with the ratchet end 50 of the first washer. As the handle 18 is turned, the ratchets on the ratchet washer 52 and first spiral washer 40 engage one another, causing the first spiral washer 40 to rotate. Because the second spiral washer 42 is fixed, the two spiral ramps 44, 46 engage and cause the first spiral washer 40 to become raised (by a height D) relative to the second spiral washer 42.

Figure 7:
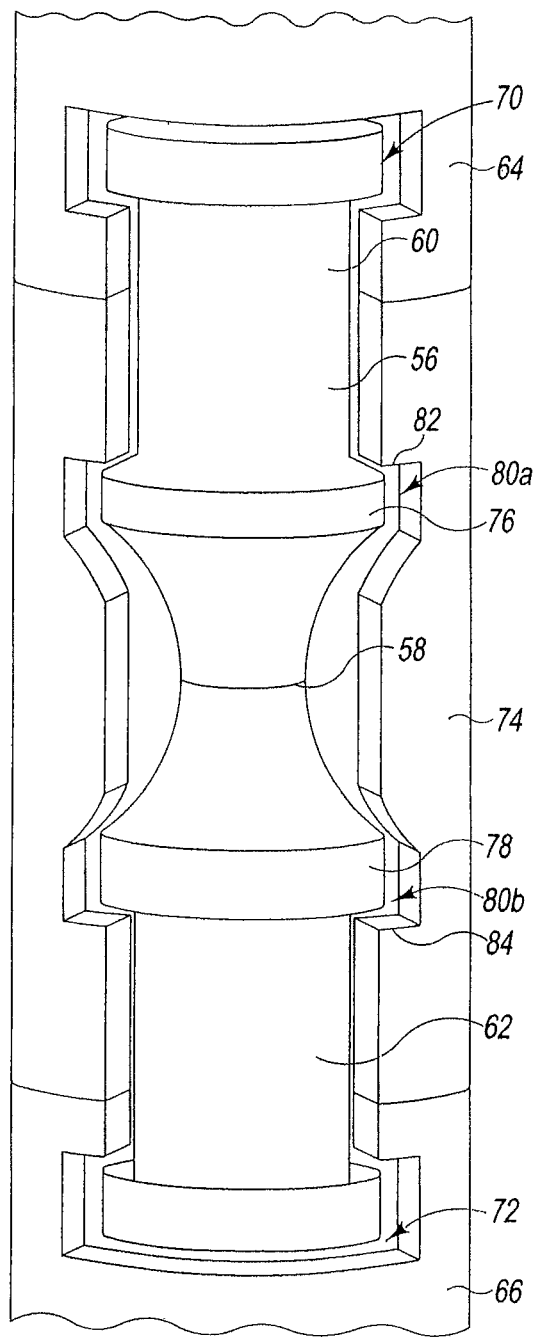
FIG. 7 is a cut-away view of a tensile rod assembly of the assembly tool of FIG. 1.

Referring still to FIG. 4 and also to FIG. 7, the second member 14 includes a sacrificial member 56, which in this case is a tensile rod or shear pin. The tensile rod 56 includes an intentional weak spot or breakage point 58. The breakage point 58 can only tolerate up to a specific tension. After that load (or tension) is reached, the breakage point 58 breaks, leaving two separate pieces 60, 62. As shown in FIG. 4, the tensile rod 56 links an upper part 64 of the second member 14 to a lower part 66 of the second member 14. As the handle 18 is turned, and the threaded distal end 32 of the second member 14 is threaded into the threaded bore of the proximal end 34 of the stem component 26, tension is created.

At the top of the upper part 64 of the second member 14, there is the knob 68, as described above. The knob 68 is turned to first thread the threaded end 32 of the second member 14 to the stem component 26.

Figure 7A:
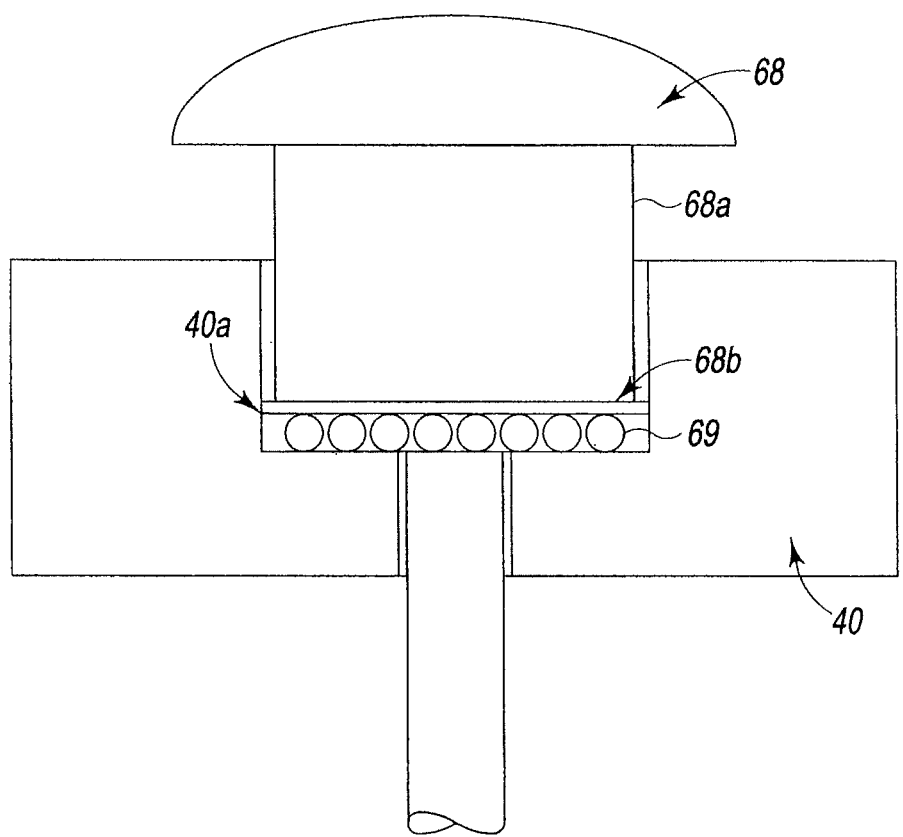
FIG. 7a is a close-up view of a washer system and a pull rod according to one embodiment of the present invention.

The knob 68 is coupled to the first spiral washer 40 in any number of known methods. In one embodiment illustrated in FIG. 7a, the knob 68 includes a pull rod 68a having a shoulder 68b. The shoulder 68b is coupled to a counterbore 40a in the first spiral washer 40, such that as the first spiral washer 40 rotates and moves upwards along the longitudinal axis 22, the knob 68 also moves upwards. In this embodiment, a bearing 69 is located between the shoulder 68b and the counterbore 40a. The bearing 69 illustrated is a rolling bearing and reduces the friction and torsional force felt by the pull rod 68a (and thus the sacrificial member 56). By reducing the frictional and torsional forces felt by the sacrificial member 56, the linear force at which the sacrificial member 56 will break is kept more consistent. In other embodiments, other types of bearings may be used. In some embodiments, no bearing 69 may be used and the shoulder 68b abuts the counterbore 40a directly.

As stated above, as the first spiral washer 40 rotates, and moves up along the longitudinal axis 22, the knob 68 also moves upwards. Because the knob 68 and threaded end 32 are coupled to one another and the threaded end is fixed within the stem component, the movement of the knob 68 creates tension along the second member 14. Once the tension reaches a certain force (or load), the tensile rod 56 will break at the breakage point 58. A loud noise will be heard; also the knob 68 will become loose. The tensile rod 56 breaking is important because it signals to the user that enough force has been applied. In this embodiment, the tensile rod 56 is fixed to break at a predetermined force. In some embodiments, that force is between about 2000 lbf and about 2500 lbf, and preferably at about 2250 lbf. In some embodiments, the knob 68 may also be used to disengage the ratchet washer 52 from the ratchet end 50 of the first washer 40.

As shown in FIG. 7, the two halves 60, 62 of the tensile rod 56 are each fitted into slotted openings 70, 72, respectively, of the second member 14. A sleeve 74 fits around the tensile rod 56. As shown, the first half 60 and the second half 62 each include a rib 76, 78 respectively, that extends outwardly. The ribs 76, 78 each fit within a recess 80a, 80b of the sleeve 74. The ribs 76, 78 also engage an edge 82, 84 of the recesses 80a, 80b. Once the tensile rod 56 breaks, both the first and second halves 60, 62 remain contained within the sleeve 74. Even though the first and second halves 60, 62 are no longer connected directly to one another, rotation of one will cause the other to rotate. As the knob 68 is rotated, the slotted opening 70 rotates. This rotation causes the first half 60 of the tensile rod 56 to rotate. When the first half 60 rotates, it engages the edge 82 of the sleeve 74, causing the sleeve 74 to rotate. As the sleeve 74 rotates, the edge 84 engages the second half 62, causing the second half 62 to rotate. The second half 62 rotating engages the slotted opening 72, causing the lower portion 66 of the second member 14 to rotate, disengaging the threaded end 32 from the stem component 26. In another embodiment, the two halves 60, 62 of the tensile rod 56 are keyed together, such that even after the halves 60, 62 break, they are still coupled together. Then, when one half rotates, the other half also is forced to rotate.

In the above embodiment, the tensile rod 56 is held by the second member. However, in other embodiments, it may be held by the first member. Also, any known containment method may be used. Alternatively, the tensile rod 56 need not be contained.

In some embodiments, the sacrificial member 56 may not be a tensile rod, but could be a torsional member. Once loads are applied on a longitudinal axis, the torsional member feels rotational force (e.g., a torsional spring). The torsional spring could be weakened so as to break at a certain force. In other embodiments, the sacrificial member 56 could be designed to fail in both axial and torsional directions.

Generally, the assembly tool 10 may be made from stainless steel. In some embodiments, the tensile rod 56 are made from 440C stainless steel, while all other components are made from 17-4 stainless steel. In other embodiments, the assembly tool 10 may be made of plastic, with only the washer system 16 and the tensile rod 56 being made of stainless steel. In other embodiments, other metals may be used. The tensile rod 56 could be made from plastic, ceramic, or other polymer. In other embodiments, the sleeve 74 could also be made of plastic or other polymer. In other embodiments, the assembly tool 10 may entirely be made of a single composite material. In some embodiments, the tensile rod 56 could be a small fixture with a shear pin.

In some embodiments, the distal end 28 of the first member 12 could include dimples that would create impressions on the proximal end of the neck component 24. The impressions would serve as a direct correlation to the force applied to the modular construct, much like those produced by a Rockwell hardness test machine. The spherical dimples on 28 could be positioned (clocked), such that, 3-impressions would be created in each use, regardless of the instrument-to-implant orientation. The physical size of the dimples would be predetermined, based on the material hardness of the proximal body. Other dimension (other than spherical) dimples could also be used. Alternatively, a number other than three dimples may be used.

In some embodiments, there may be a biasing mechanism, such as a wave spring or other type of spring, used to keep the ratchet washer 52 engaged with the ratchet end 50 of the first washer 40. Other springs may be used in the device to cause the first washer 40 to spring back after being ratcheted. In some embodiments, the spring may be a constant force spring.

Figure 8:
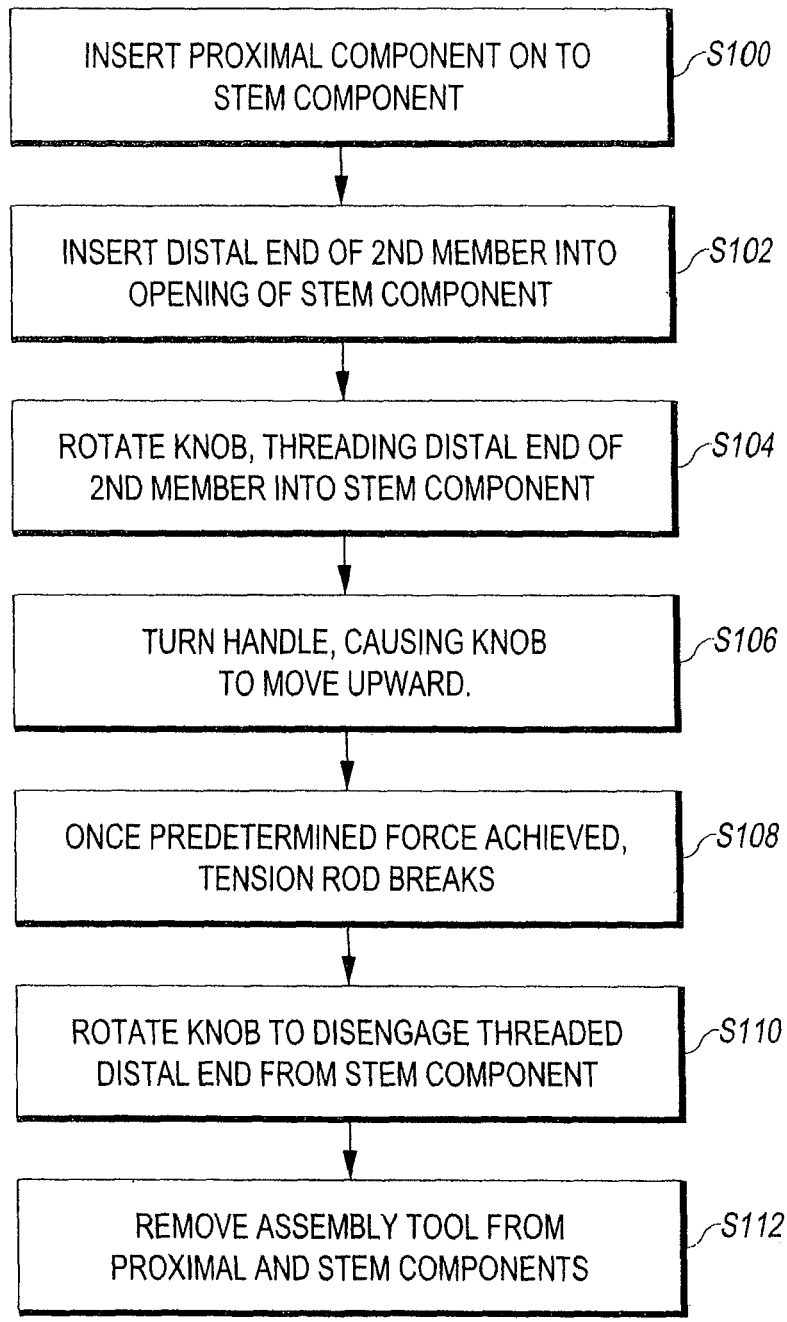
FIG. 8 is a flow chart of the method for using the assembly tool according to one embodiment of the present invention.

Turning now to FIG. 8, a flow chart describing the method of using the assembly tool 10 is shown. As shown, at step s100, the proximal component is inserted on to the stem component. Then the distal end of the second member is inserted into the opening of the stem component at step s102. When this is achieved, the distal end of the first member abuts the proximal end of the first component. At step s104, the knob is rotated threading the distal end of the second member into the stem component. The drive mechanism is then turned, causing the knob to move upward (step s106), as described above. Once a predetermined force is applied, the tensile rod breaks, indicating that the proper force has been applied (step s108). At step s110, the knob is rotated to disengage the threaded distal end from the stem component and the assembly tool is removed from the proximal and stem components (step s112).

Figure 9:
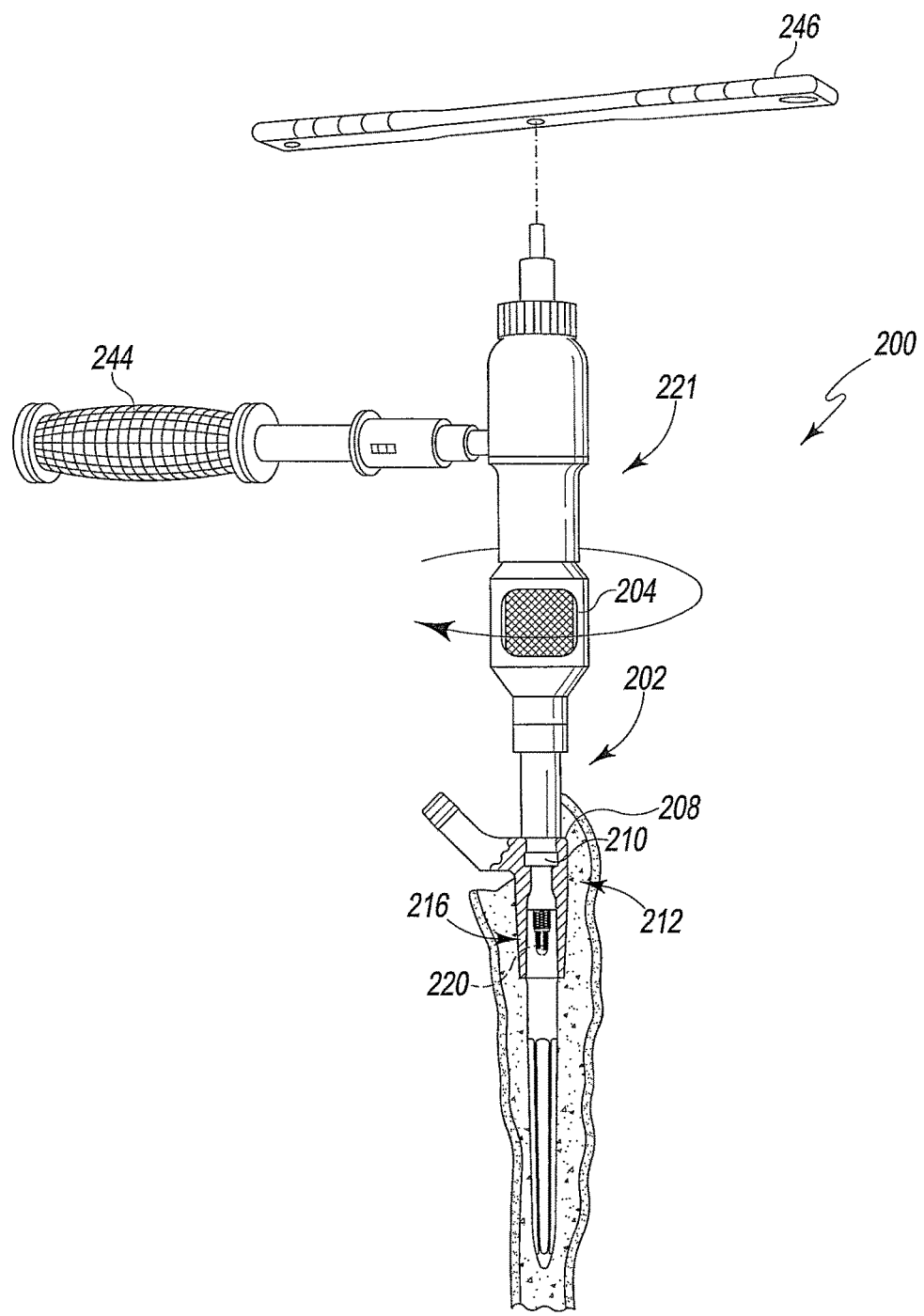
FIG. 9 is a partial see-through perspective view of an assembly tool according to one embodiment of the present invention.
Figure 10:
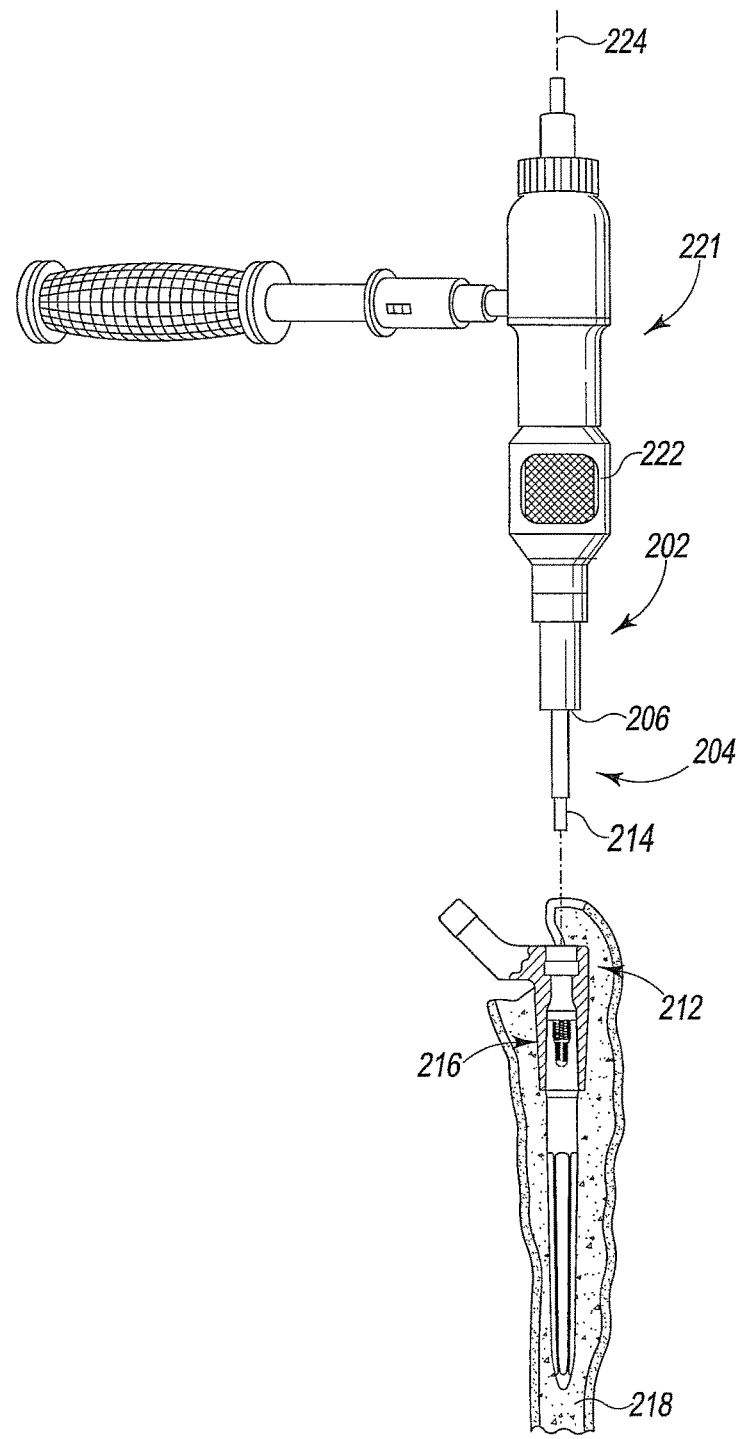
FIG. 10 is another perspective view of the assembly tool of FIG. 9.

Turning now to FIGS. 9 and 10, another embodiment of the present invention will be illustrated. In FIG. 9, a perspective view of an assembly tool 200 is shown. The assembly tool 200 includes a first member 202 and a second member 204. The first member 202 includes a distal end 206 (FIG. 10) that abuts a proximal end 208 of a neck component 210 of an implant 212. Alternatively, the connection means may be a retractable button/recess system, a slotted 1-shaped recess and rod system, an undercut, an expandable collet system, or any other known engagement system.

A distal end 214 of the second member 204 engages a proximal end 216 of a stem component 218. In this embodiment, the distal end 214 of the second member 204 is threaded and fits inside a threaded bore of the proximal end 220 of the stem component 218. Alternatively, the distal end 214 of the second member 204 may have the threaded bore and the proximal end 216 of the stem component 218 may be threaded. In other embodiments, other known means of connecting pieces may be used. For example, an expandable collet may be used. Alternatively, the connection means may be a retractable button/recess system, an undercut, a slotted 1-shaped recess and rod system, an expandable collet system, or any other known engagement system.

The second member 204 also includes a proximal end 221. The proximal end 221 includes a knob 222. The knob 222 is coupled to the threaded distal end 214, such that as the knob 222 is rotated about a second member longitudinal axis 224, the threaded distal end 214 is threaded into the threaded bore proximal end 220 of the stem component 218.

Figure 11:
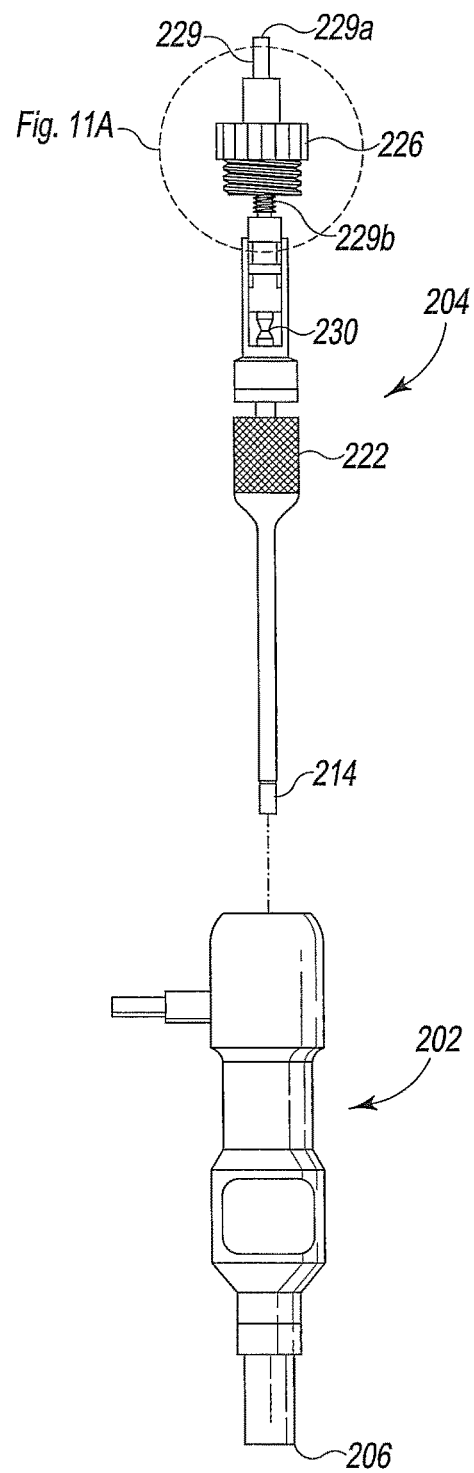
FIG. 11 is a partially exploded view of the assembly tool of FIG. 9.
Figure 12:
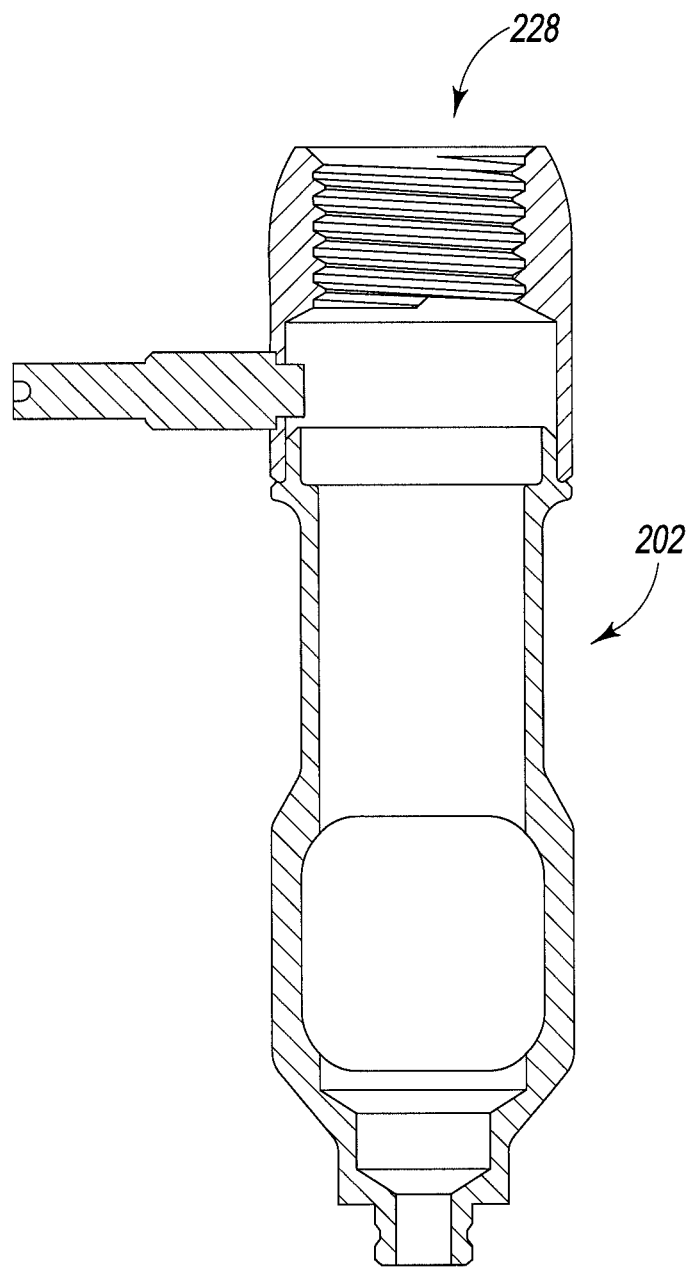
FIG. 12 is a cut-away view of a first member of the assembly tool of FIG. 9.

Turning now to FIG. 11, an exploded view of the assembly tool 200 is illustrated. As shown, the second member 204 is shown disassembled from the first member 202. The second member 204 includes a threaded cap 226. When assembled, the threaded cap 226 is threaded into a corresponding threaded bore 228 (FIG. 12).

Figure 11A:
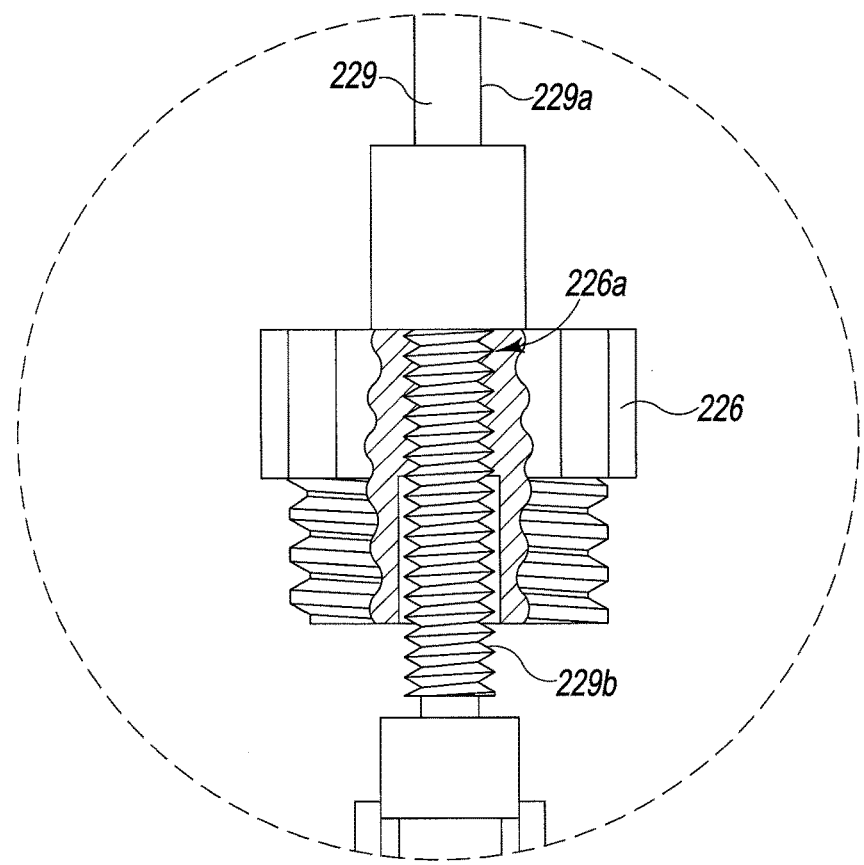
FIG. 11a is a close-up view of a portion of the assembly tool of FIG. 11.

As shown in FIGS. 11 and 11a, a rod 229 having a hex end 229a and a threaded end 229b is shown. The rod 229 is threaded into a threaded recess 226a of the cap 226. The male threads of the threaded end 229b are made of stainless steel, such as 455 custom stainless steel and the cap 226 (including its female threads 226a) are made of a Stainless Steel, such as Nitronic 60. 455 custom stainless steel is a hard material, while Nitronic 60 is comparably very soft. Thus, when the two are moved relative to one another, there is very little galling and the parts can be cycled a number of times before having to be replaced. The second member 204 also includes a tensile bar 230 that is sized and shaped to break at a predetermined force. This informs the user when the correct force has been reached. In some embodiments, that force is between about 2000 lbf and about 2500 lbf.

Figure 13:
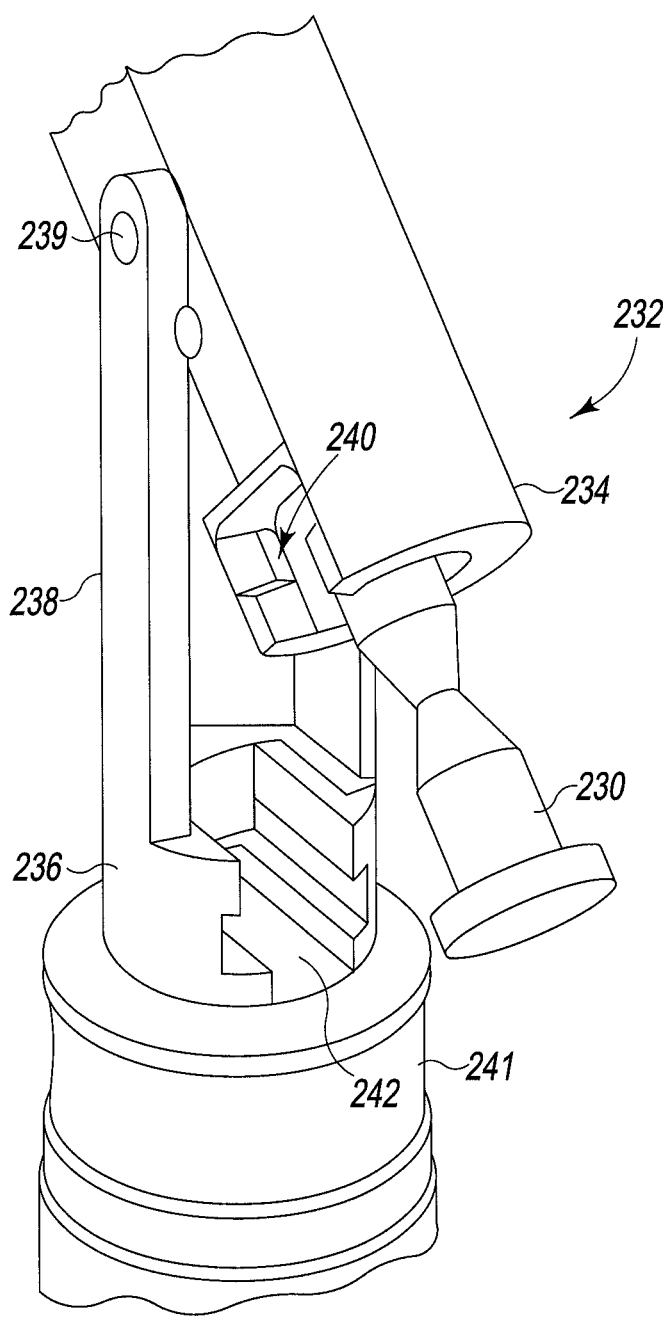
FIG. 13 is a perspective view of a tensile bar and housing of the assembly tool of FIG. 9.

As shown in FIG. 13, the tensile bar 230 is held into place by a housing 232. The housing 232 includes an upper restraint 234 and a lower restraint 236. The upper restraint 234 is pivotally attached to the lower restraint 236 by extension arms 238 on the lower restraint and pivot pins 239. The upper restraint 234 includes a t-shaped slot 240 that is shaped to engage the tensile bar 230. The opening of the t-shaped slot 240 faces one of the extension arms 238. The lower restraint 236 includes a t-shaped slot 242, with the opening facing perpendicular from the opening of the t-shaped slot 240 of the upper restraint 234. The lower restraint 236 also includes a spring-loaded lower section 241.

In use, the user would pull down on the spring-loaded lower section 241, and pivot the upper restraint 234 into an open position. The user then inserts the tensile bar 230 into the t-shaped slots. The upper restraint 234 is then pivoted back into alignment with the lower restraint 236 and the user releases the spring-loaded lower section 241. The opening of the t-shaped slot 240 of the upper restraint 234 is blocked by one of the extension arms and the opening of the t-shaped slot 242 of the lower restraint 236 is blocked by the released spring-loaded lower section 241.

During use, once the tensile bar 230 breaks, the t-shaped openings 240, 242 keep the respective halves of the tensile bar 230 in place along with the spring-loaded lower section 241 until the user is ready to disassemble the tool 200. Also, as described above in reference to assembly tool 10, the upper and lower restraints 234, 236 are keyed together, so that even after the tensile bar breaks, the upper and lower restraints 234, 236 still move together.

Returning now to FIGS. 9 and 10, the use of the assembly tool 200 will be described. As shown, the first member 202 includes a stationary handle 244 and a torque handle 246 is inserted onto the second member 204. To use, the assembly tool 200 is inserted into the proximal body 208 such that the distal end 206 of the first member abuts the proximal body 208. The distal end 214 of the second member is inserted into the threaded opening 220 of the stem 218 and the knob 222 of the second member 204 is rotated, causing the threaded distal end 214 of the second member 204 to threadingly engage the threaded opening 220 of the stem 218. The user then rotates the torque handle 246 while holding the handle 244 of the first member 202 stationary. During this use, the rod 229 is rotated relative to the cap 226 and the threaded end 229a is moved relative to the cap 226, thereby moving the threaded distal end 214. The user continues to rotate until an audible sound is heard, indicating the breaking of the tensile bar 230. The user then disengages the tool 200 from the implant by rotating the knob 222 counterclockwise.

Although the present invention and its advantages have been described in detail, it should be understood that various changes, substitutions, and alterations can be made therein without departing from the spirit and scope of the present invention as defined by the appended claims.

We claim:

1. An assembly tool for assembly of a first component of a prosthesis to a second component of the prosthesis for use in joint arthroplasty, the tool comprising: a first member operably associated with the first component; and a second member operably associated with the second component; wherein the second member includes a cap having a threaded recess and further includes a threaded rod configured to engage the threaded recess so as to move the second member relative to the first member and the threaded rod is made of a harder metal than the threaded recess, wherein the second member includes a tensile bar that is sized and shaped to break at a predetermined force and the second member includes a housing configured to house the tensile bar, the housing including an upper restraint, a lower restraint, and a pivot pin coupling the upper restraint to the lower restraint, and the lower restraint including a slot, such that when the upper restraint is pivoted via the pivot pin, the tensile bar swings out of the slot in the lower restraint.

2. The assembly tool of claim 1, wherein the threaded recess of the cap is made of a Nitinol and the threaded rod is made of a stainless steel.

3. The assembly tool of claim 2, wherein the threaded recess of the cap is made of Nitronic 60 and the threaded rod is made of 455 custom stainless steel.

4. The assembly tool of claim 1, wherein the predetermined force is between about 2000 lbf and about 2500 lbf.

5. The assembly tool of claim 1, wherein the upper restraint includes a t-shaped slot having an opening configured to receive the tensile bar.

6. The assembly tool of claim 5, wherein the slot of the lower restraint is a t-shaped slot having an opening perpendicular to the opening of the t-shaped slot of the upper restraint.

7. An assembly tool for assembly of a first component of a prosthesis to a second component of the prosthesis for use in joint arthroplasty, the tool comprising: a first member operably associated with the first component, the first member defining a first member longitudinal axis thereof; a second member operably associated with the second component, including a tensile bar configured to break at a predetermined force, wherein the second member includes a housing configured to retain the tensile bar after the tensile bar breaks, wherein the housing including an upper restraint, a lower restraint, and a pivot pin coupling the upper restraint to the lower restraint, and the lower restraint including a slot, such that when the upper restraint is pivoted via the pivot pin, the tensile bar swings out of the slot in the lower restraint.

8. The assembly tool of claim 7, wherein the predetermined force is between about 2000 lbf and about 2500 lbf.

9. The assembly tool of claim 7, wherein the upper restraint includes a t-shaped slot having an opening configured to receive the tensile bar.

10. The assembly tool of claim 9, wherein the slot of the lower restraint is a t-shaped slot having an opening perpendicular to the opening of the t-shaped slot of the upper restraint.

11. The assembly tool of claim 7, wherein the lower restraint includes a spring-loaded lower section configured to contain the tensile bar in the lower restraint.

12. The assembly tool of claim 7, wherein the second member includes a cap having a threaded recess and further includes a threaded rod configured to engage the threaded recess so as to move the second member relative to the first member and the threaded rod is made of a harder metal than the threaded recess.

13. The assembly tool of claim 12, wherein the threaded recess of the cap is made of a Nitinol and the threaded rod is made of a stainless steel.

14. The assembly tool of claim 13, wherein the threaded recess of the cap is made of Nitronic 60 and the threaded rod is made of 455 custom stainless steel.

* * * * *